United States Patent [19]

Kumagai et al.

[11] Patent Number: 5,077,971
[45] Date of Patent: Jan. 7, 1992

[54] AIR/FUEL RATIO CONTROL SYSTEM FOR AN INTERNAL COMBUSTION ENGINE

[75] Inventors: Shiro Kumagai; Katsuo Akishino, both of Kyoto; Reijiro Komagome, Joyo; Michiyasu Yoshida, Kyoto; Tateo Kume, Kameoka; Masaki Nishizawa, Kyoto; Seiji Ishida; Takehisa Fujita, both of Kyoto, all of Japan

[73] Assignee: Mitsubishi Jidosha Kogyo Kabushiki Kaisha, Tokyo, Japan

[21] Appl. No.: 544,731

[22] Filed: Jun. 27, 1990

[30] Foreign Application Priority Data

Jun. 27, 1989 [JP] Japan ................................ 1-166341

[51] Int. Cl.$^5$ ............................................. F02D 41/14
[52] U.S. Cl. ...................................... 60/276; 60/285; 123/489
[58] Field of Search .................. 123/440, 489, 589; 60/276, 285

[56] References Cited

U.S. PATENT DOCUMENTS

| 4,156,413 | 5/1979 | Taplin ................................ 60/276 |
| 4,809,501 | 3/1989 | Kayanuma et al. ................ 123/489 |
| 4,926,828 | 5/1990 | Fujimoto et al. .................. 123/440 |

Primary Examiner—E. Rollins Cross
Assistant Examiner—Robert E. Mates
Attorney, Agent, or Firm—Wegner, Cantor, Mueller & Player

[57] ABSTRACT

An air/fuel ratio control system is provided for use with an internal combustion engine. The system includes an air/fuel ratio detector arranged on an upstream side of a catalytic converter so as to detect the air/fuel ratio of the internal combustion engine from components of exhaust gas, a device for controlling the air/fuel ratio of the internal combustion engine on the basis of results of a comparison between a detection value from the air/fuel ratio detector and a predetermined reference value; and a device for shifting the reference value to a lean air/fuel ratio side in a specific operation state of the internal combustion engine.

13 Claims, 39 Drawing Sheets

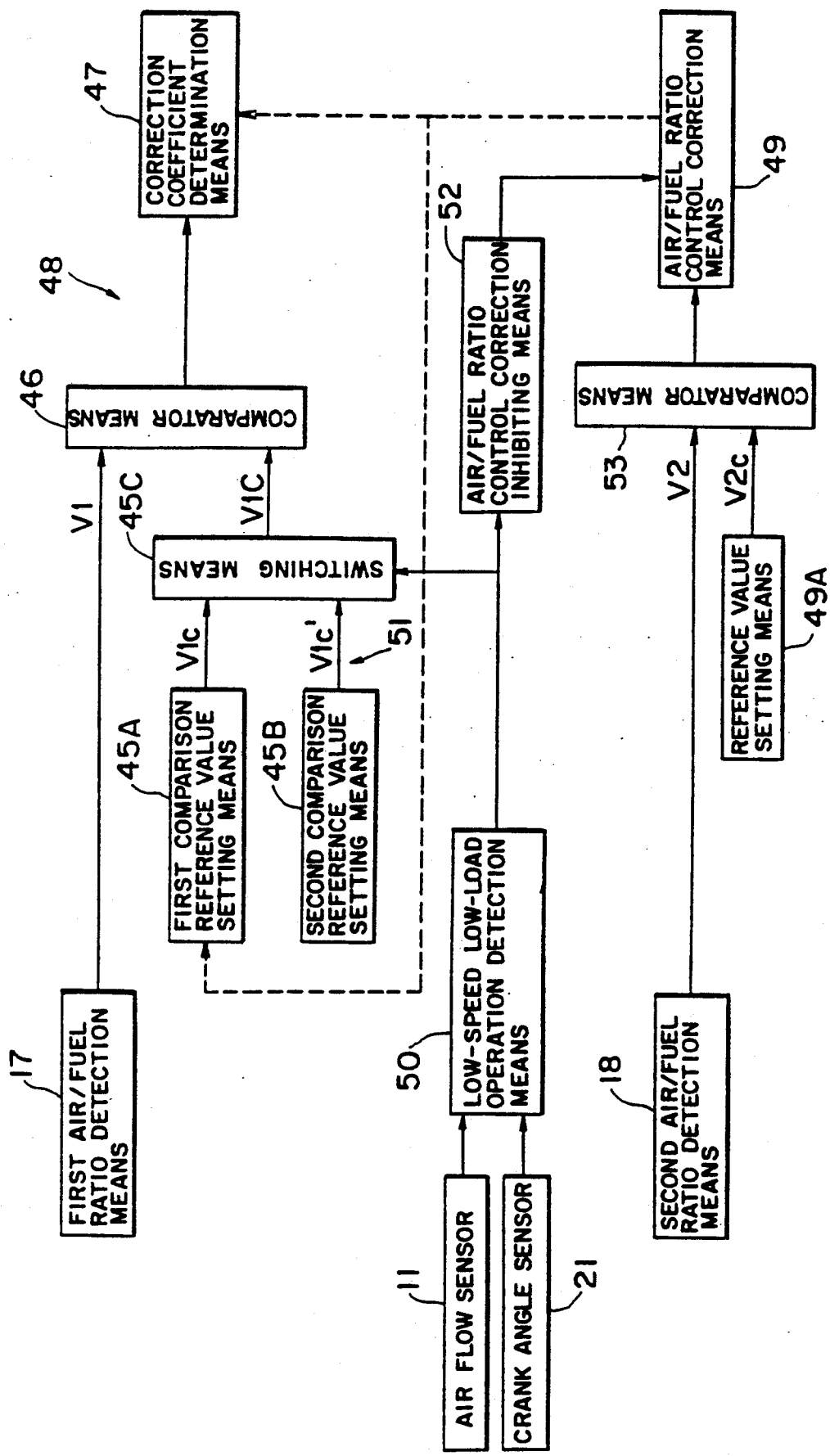
FIG. I(a)

FIG.20(a)
FIG.20(b)
FIG.20(c)
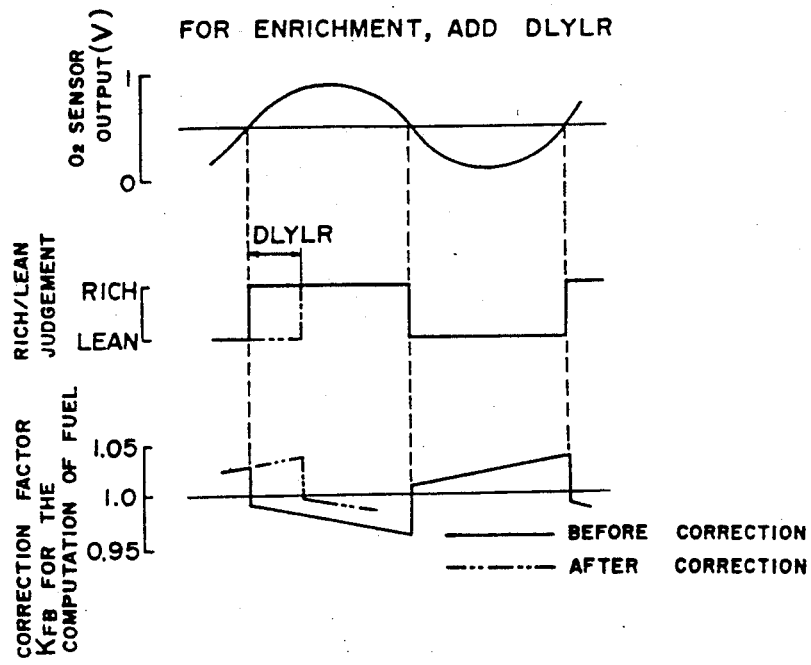
FIG.21(a)
FIG.21(b)
FIG.21(c)
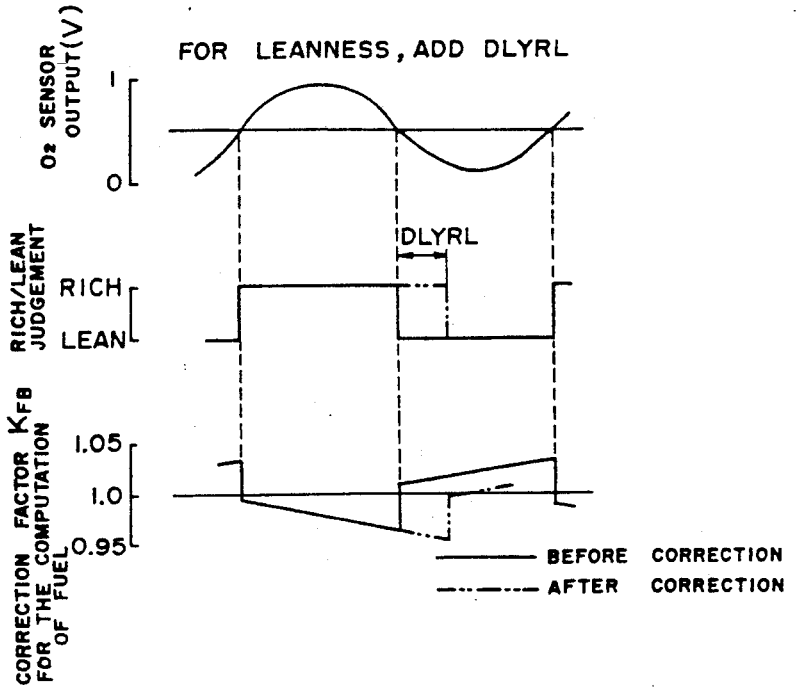

FIG.22(a)
FIG.22(b)
FIG.22(c)
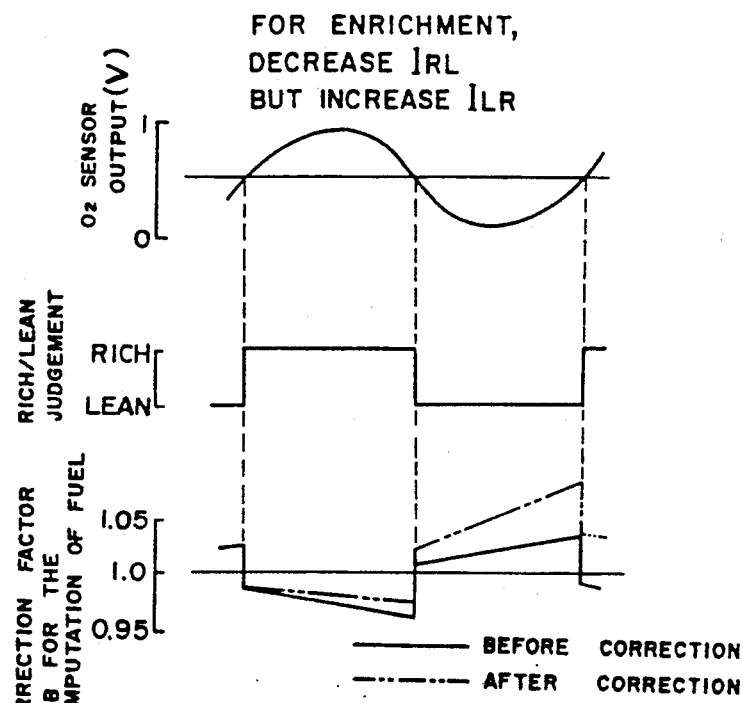
FIG.23(a)
FIG.23(b)
FIG.23(c)
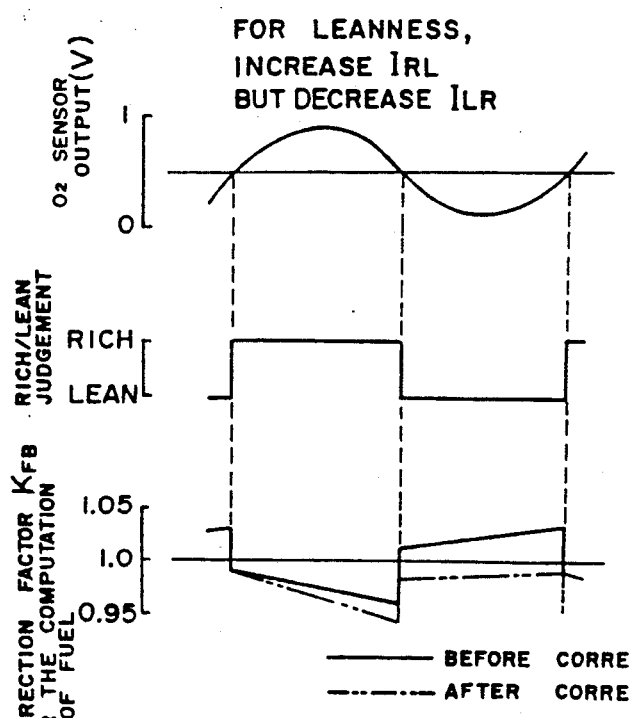

FIG.24(a)
FIG.24(b)
FIG.24(c)
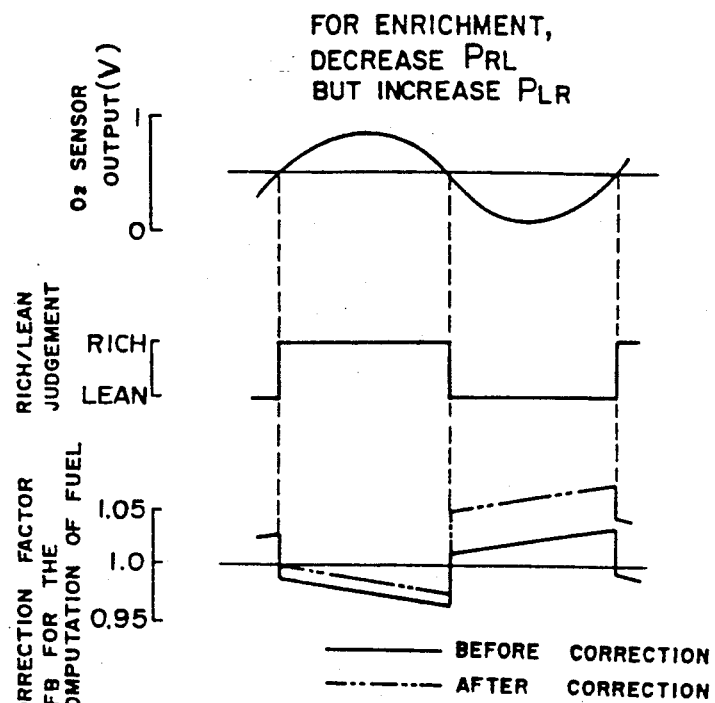
FIG.25(a)
FIG.25(b)
FIG.25(c)
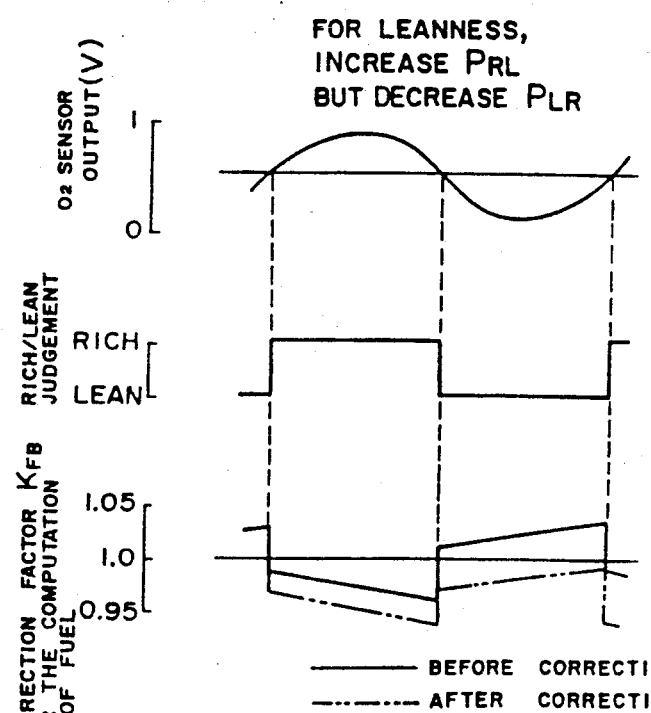

AIR/FUEL RATIO CONTROL SYSTEM FOR AN INTERNAL COMBUSTION ENGINE

BACKGROUND OF THE INVENTION

1. Field of the Invention

This invention relates to an air/fuel ratio control system for an internal combustion engine the air/fuel ratio of an internal combustion which may hereinafter also be called an "engine" as needed.

2. Description of the Related Art

An exhaust gas purifying system is conventionally known wherein a three-way catalyst for purifying exhaust gas of an internal combustion engine is disposed in an exhaust system of the internal combustion engine to purify exhaust gas of the engine.

It is already known that the exhaust gas purifying efficiency of such an exhaust gas purifying system can be improved by fluctuating the air/fuel ratio around the theoretical air/fuel ratio.

To this end, an oxygen concentration sensor of the λ type (which denotes an oxygen concentration sensor which presents a sudden change in output value thereof around a predetermined air/fuel ratio (theoretical air/fuel ratio, and such sensor will be hereinafter referred to as $O_2$ sensor) is conventionally provided in an exhaust manifold, i.e., on an forward side of a catalytic converter. Interested with the fact that the output of such $O_2$ sensor presents a change from an on-state to an off-state, that is, a change from a high voltage level to a low voltage level or vice versa across the predetermined air/fuel ratio (theoretical air/fuel ratio), the output of the $O_2$ sensor is fed back to control the air/fuel ratio so that the air/fuel ratio may remain around the theoretical air/fuel ratio. Such control is called $O_2$ feedback control.

In such $O_2$ feedback control, an output of the $O_2$ sensor is compared with an on/off threshold voltage (reference value), and if, for example, the $O_2$ sensor output is higher than the threshold voltage, the air/fuel ratio is controlled toward the lean side, but on the contrary, if the $O_2$ sensor output is lower than the threshold voltage, the air/fuel ratio is controlled toward the rich side.

It has recently been proposed to provide an additional $O_2$ sensor on the rearward side of the catalytic converter provided in the engine exhaust system (This $O_2$ sensor will hereinafter be called "rearward $O_2$ sensor" while an $O_2$ sensor provided on the forward side of the catalytic converter like the above-described $O_2$ sensor will be called an "forward $O_2$ sensor") and to information for the control of the air/fuel ratio (so-called dual $O_2$ sensor system or double $O_2$ sensor system). Even in this case, a standard value which should be compared with an output from the rearward $O_2$ sensor will not be changed once it has been set.

It has also been proposed to arrange an $O_2$ sensor, which has a slow detection response speed, on an forward side of a catalytic converter disposed in an engine exhaust system and to use an output from the $O_2$ sensor as information for the correction of control of the air/fuel ratio.

Such conventional means however involve the following problems when the output of the $O_2$ sensor indicates a rich air/fuel ratio as a result of control by the $O_2$ sensor and the timing of acceleration in a small intake-air-quantity operation state (low-speed and low-load operation state, low-load operation state, idling state, or the like) before acceleration [see FIG. 52(a), point a1]. Since the catalytic converter is in an oxygen-deficient state before such acceleration, acceleration as shown in FIG. 52(c) in such a state leads to the problem that the emission of HC and CO increases immediately after the acceleration [see the characteristic curve shown by a solid line in FIG. 52 (b). In addition, the catalytic converter is brought into an oxygen-excessive lean state because of the control by the $O_2$ sensor after the acceleration [see FIG. 52(a), point a2]. This results in a reduction to the efficiency of purification of NOx, so that more NOx is emitted as shown by the dashed characteristic curve in FIG. 52(b).

SUMMARY OF THE INVENTION

With a view toward overcoming the foregoing problems, the present invention has as a principal object thereof the provision of an air/fuel ratio control system for an internal combustion engine, said air/fuel ratio control system being of the type that the air/fuel ratio of the internal combustion engine is controlled by the results of a comparison between a detection value from an air/fuel ration detection means arranged on an forward side of at least a catalytic converter and a predetermined reference value, in which the reference value can be shifted to a lean air/fuel ratio side in a specific operation state such as a small intake-air-quantity operation state so as to avoid deterioration of the purifying efficiency for HC, CO and NOx by the catalytic converter even when the internal combustion engine is accelerated from the specific operation state.

In a first aspect of the present invention, there is thus provided an air/fuel ratio control system for an internal combustion engine, comprising:

a first air/fuel ratio detection means arranged on an forward side of a catalytic converter so as to detect the air/fuel ratio of the internal combustion engine from components of exhaust gas, said catalytic converter being provided in an exhaust system of the internal combustion engine and adapted to clean the exhaust gas;

a second air/fuel ratio detection means arranged in the exhaust system and having a detection response speed slower than the said air/fuel ratio detection means;

a means for controlling the air/fuel ratio of the internal combustion engine on the basis of results of a comparison between a detection value from said first air/fuel ratio detection means and a predetermined first reference value;

a means for effecting a correction to the control of the air/fuel ratio by said air/fuel ratio control means on the basis of results of a comparison between a detection value from said second air/fuel ratio detection means and a predetermined second reference value;

a means for shifting the first reference value to a lean air/fuel ratio side in a specific operation state of the internal combustion engine; and a means for prohibiting the correction by the air/fuel ratio controlling means in the specific operation state.

According to the air/fuel ratio control system of the first aspect of the present invention, the air/fuel ratio of the internal combustion engine is controlled by the air/fuel ratio control means on the basis of the results of a comparison between a detection value from the first air/fuel ratio detection means and the first reference value and, further, a correction is made to the control of the air/fuel ratio by the air-fuel ratio control means on the basis of the results of a comparison between a detection value from the second air/fuel ratio detection means and the second reference value. In a specific operation state of the internal combustion engine, for example, in a small intake-air-quantity operation state, the first reference value to be compared with the detection value from the first air/fuel ratio detection means is shifted to the lean air/fuel ratio side and the correction by the correction means for the air/fuel ratio control is prohibited.

The air/fuel ratio control system of the first aspect of the present invention can therefore bring about advantages such that the accuracy of the control is not changed by variations in characteristics of each air/fuel ratio detection means such as an $O_2$ sensor and changes of its characteristics along the passage of time, the efficiency of cleaning of exhaust gas by the catalytic converter can be maintained high, and high reliability is thus assured in regard to the control; the efficiency of purification for HC, CO and NOx by the catalytic converter is not deteriorated even when the internal combustion engine is accelerated from a specific operation state such as a small intake-air-quantity operation state; and the provision of the correction-prohibiting means makes it possible not to impair the high reliability of the control.

In a second aspect of the present invention, there is also provided an air/fuel ratio control system for an internal combustion engine, comprising:

an air/fuel ratio detection means arranged on an forward side of a catalytic converter so as to detect the air/fuel ratio of the internal combustion engine from components of exhaust gas, said catalytic converter being provided in an exhaust system of the internal combustion engine and adapted to clean the exhaust gas;

a means for controlling the air/fuel ratio of the internal combustion engine on the basis of results of a comparison between a detection value from said air/fuel ratio detection means and a predetermined reference value; and a means for shifting the reference value to a lean air/fuel ratio side in a specific operation state of the internal combustion engine.

According to the air/fuel ratio control system of the second aspect of the present invention, the air/fuel ratio of the internal combustion engine is controlled by the air/fuel ratio control means on the basis of the results of a comparison between a detection value from the air/fuel ratio detection means and the predetermined reference value. In a specific operation state of the internal combustion engine, for example, in a small intake-air-quantity operation state, the reference value to be compared with the detection value from the air/fuel ratio detection means is shifted to the lean air/fuel ratio side.

The air/fuel ratio control system of the second aspect of the present invention can therefore bring about the advantage that the efficiency of purification for HC, CO and NOx by the catalytic converter is not deteriorated even when the internal combustion engine is accelerated from a specific operation state such as a small intake-air-quantity operation state while performing the feedback control.

BRIEF DESCRIPTION OF THE DRAWINGS

The above and other objects, features and advantages of the present invention will become apparent from the following description and the appended claims, taken in conjunction with the accompanying drawings, in which:

FIGS. 1(a) through 29 illustrate an air/fuel ratio control system according to a first embodiment of this invention, which is suitable for use with an internal combustion engine, in which:

FIG. 1(a) is a fragmentary block diagram of the control system;

FIG. 2 is a block diagram of the control system, which depicts its hardware primarily;

FIG. 3 is a schematic illustration showing an overall engine system;

FIG. 4 is a flow chart for illustrating a main routine of the control system;

FIG. 5 is a flow chart for describing a solenoid valve drive routine for the control system;

FIG. 6 is a flow chart for illustrating an integration time computing routine for the control system;

FIG. 7 is a flow chart for determining the deviation of an output of a rearward $O_2$ sensor in the control system from a target value;

FIG. 8 is a flow chart for correcting a response delay time on the basis of the deviation determined in FIG. 7;

FIG. 9 is a flow chart for correcting, based on the deviation determined in FIG. 7, an integral gain for the air/fuel ratio feedback control;

FIG. 10 is a flow chart for correcting, based on the deviation determined in FIG. 7, a proportional gain for the air/fuel ratio feedback control;

FIG. 11 is a flow chart for correcting, based on the deviation determined in FIG. 7, a first reference value for rich/lean judgment to be compared with an output from an forward $O_2$ sensor;

FIGS. 12(a–c) are a graph for illustrating an air/fuel ratio feedback factor for the control system;

FIGS. 20(a–c) and 21(a–c) are respectively graphs for describing a correction method which relies upon the response delay time;

FIGS. 22(a–c) and 23(a–c) are respectively graphs for describing a correction method which relies upon the integral gain for the air/fuel ratio feedback control;

FIGS. 24(a–c) and 25(a–c) are respectively graphs for describing a correction method which relies upon the proportional gain for the air/fuel ratio feedback control;

FIGS. 26(a–c) and 27(a–c) are respectively graphs for describing a correction method which relies upon the reference value for rich/lean judgment to be compared with the output from the forward $O_2$ sensor;

FIG. 29 diagrammatically shows the relationship among HC, CO and NOx in both the first embodiment and a conventional example;

FIGS. 30 and 31 show an air/fuel ratio control system according to a second embodiment of this invention, which is suitable for use with an internal combustion engine, in which:

FIG. 30 is a flow chart for illustrating a main routine of the control system; and FIG. 31 is a flow chart for determining a correction value on the basis of the deviation determined in FIG. 7;

FIGS. 32 and 46 illustrate an air/fuel ratio control system according to a third embodiment of this invention, which is suitable for use with an internal combustion engine, in which:

FIG. 32 is a schematic illustration showing an overall engine system; and

FIGS. 33 through 46 depict $O_2$ sensors useful in the control system, in which:

FIG. 33 is a perspective view of an $O_2$ sensor;

FIG. 34 is a fragmentary perspective view of the $O_2$ sensor, in which some parts are shown in cross-section;

FIG. 35 is a fragmentary front view of the $O_2$ sensor;

FIG. 36 is a fragmentary cross-sectional view of the $O_2$ sensor;

FIG. 37 is an exploded perspective view of the $O_2$ sensor;

FIGS. 40 through 42 and 43(a-f) show another $O_2$ sensor useful in the control system, in which:

FIG. 40 is a fragmentary front view of the $O_2$ sensor;

FIG. 41 is a fragmentary cross-sectional view of the $O_2$ sensor;

FIG. 42 is a cross-sectional view of the $O_2$ sensor, taken in the direction of arrows XXXXII—XXXXII of FIG. 41.

FIGS. 44 through 46 depict a further $O_2$ sensor useful in the control system, in which:

FIG. 44 is a fragmentary front view of the $O_2$ sensor;

FIG. 45 is a fragmentary cross-sectional view of the $O_2$ sensor; and

FIG. 46 is a cross-sectional view of the $O_2$ sensor, taken in the direction of arrows XXXXVI—XXXXVI of FIG. 45;

FIGS. 47 through 51 illustrate an air/fuel ratio control system according to a fourth embodiment of this invention, which is suitable for use with an internal combustion engine, in which:

FIG. 47 is a schematic illustration showing an overall engine system;

FIG. 48 is a block diagram of the control system;

FIG. 49 is a fragmentary block diagram of the control system;

FIG. 50 is a block diagram of the control system which depicts its hardware primarily;

FIG. 51 is a flow chart for illustrating a main routine of the control system.

DESCRIPTION OF THE PREFERRED EMBODIMENTS

An air/fuel ratio control system according to a first embodiment of the present invention will hereinafter be described with reference to FIGS. 1 through 29.

Figure 3:
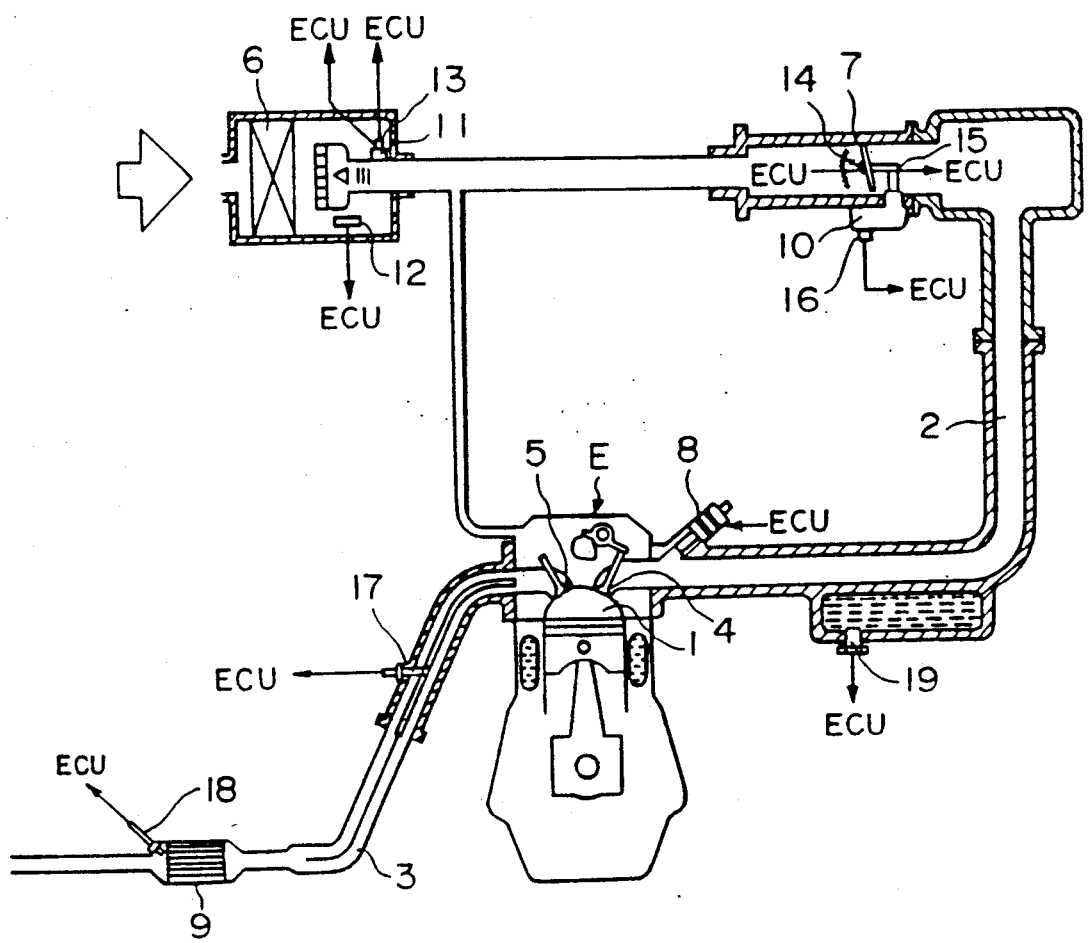

An engine system controlled by the system of this invention may be illustrated as shown in FIG. 3, in which an engine E has an intake passage 2 and an exhaust passage 3, both, communicated to a combustion chamber 1. The communication between the intake passage 2 and combustion chamber 1 is controlled by an intake valve 4, while that of the discharge passage 3 with the combustion chamber 1 is controlled by an exhaust valve 5.

In addition, the intake passage 2 is provided with an air cleaner 6, a throttle valve 7 and an electromagnetic fuel injection valve (solenoid valve) 8 in order from the forward side thereof. The exhaust passage 3 is provided with a catalytic converter (three-way catalyst) 9 for cleaning exhaust gas and an unillustrated muffler in order from the forward side thereof.

Incidentally, solenoid valves of the same type as the solenoid valve 8 are provided as many as the number of cylinders in an intake manifold portion. Let's now assume that the engine E is an in-line 4-cylinder engine in the present embodiment. Four solenoid valves 8 are hence provided. In other words, the engine E can be said to be an engine of the so-called multi-point fuel injection (MPI) system.

The throttle valve 7 is connected via an unillustrated wire cable to an accelerator pedal (not shown) so that the opening rate of the throttle valve 7 changes in accordance with the degree of depression of the accelerator pedal. In addition, the throttle valve 7 is also driven by an idling speed control motor (ISC motor), whereby the opening rate of the throttle valve 7 can be varied without need for depression of the accelerator pedal upon idling.

Owing to the above-described construction, air which has been drawn in accordance with the opening rate of the throttle valve 7 through the air cleaner 6 is mixed with a fuel from the solenoid valve 8 in the intake manifold portion so a to give a suitable air/fuel ratio. The resulting air-fuel mixture is ignited at suitable timing by an unillustrated spark plug in the combustion chamber 1, so that the air-fuel mixture is caused to burn. After producing an engine torque, the air-fuel mixture is discharged as exhaust gas into the exhaust passage 3 and subsequent to cleaning of three noxious components CO, HC, $NO_x$ in the exhaust gas by the catalytic converter 9, the exhaust gas is deadened in noise by an unillustrated muffler and then released into the surrounding atmosphere.

A variety of sensors are provided in order to control the engine E. On the side of the intake passage 2 first of all, there are provided an airflow sensor 11 for detecting the quantity of intake air from Karman vortex information, an intake air temperature sensor 12 for detecting the temperature of the air drawn and a barometric pressure sensor 13, all, in the portion where the air cleaner is provided. In a portion where the throttle valve is installed, there are provided a throttle sensor 14 of the potentiometer type, said throttle sensor 14 being adapted to detect the opening rate of the throttle valve 7, an idle switch 15 for detection the state of idling, and a motor position sensor 16 for detecting the position of the ISC motor 10.

Further, on the side of the exhaust passage 3, an forward O₂ sensor 17 for detecting the oxygen density (O₂ density) in exhaust gas, said forward O₂ sensor constituting a first air/fuel ratio detection means for detecting the air/fuel ratio of the engine E from components of the exhaust gas, is provided at a position forward of the catalytic converter 9, and a rearward O₂ sensor 18 as a second oxygen density sensor for also detecting the O₂ density in the exhaust gas is arranged at a position rearward of the catalytic converter 9.

Since the rearward O₂ sensor is provided on the rearward side of the catalytic converter 9, its detection response speed is slower compared with the forward O₂ sensor 17. Therefore, the rearward O₂ sensor 18 constitutes a second air/fuel ratio detection means whose detection response speed is slower compared with that of the forward O₂ sensor. Here, the forward O₂ sensor 17 and rearward O₂ sensor 18 both make use of the principle of oxygen concentration cells of a solid electrolyte. They have such a characteristic that their output voltages change abruptly near the stoichiometric air/fuel ratio. Their voltages are low on the side leaner than the stoichiometric air/fuel ratio but high on the side richer than the stoichiometric air/fuel ratio.

Incidentally, the rearward O₂ sensor 18 may be provided inside the catalytic converter 9.

Figure 1B:
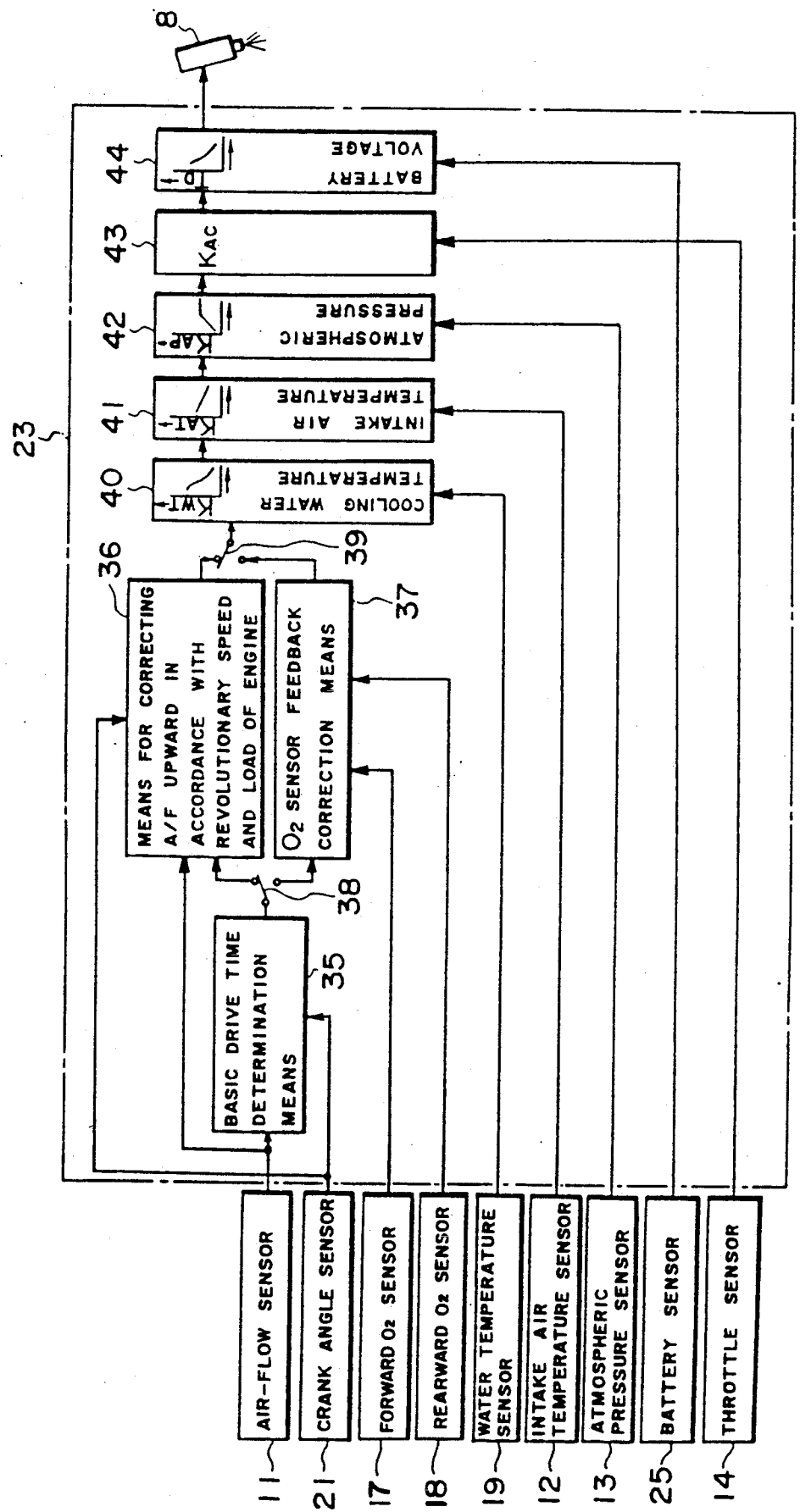
FIG. 1(b) is a block diagram of the control system.
Figure 2:
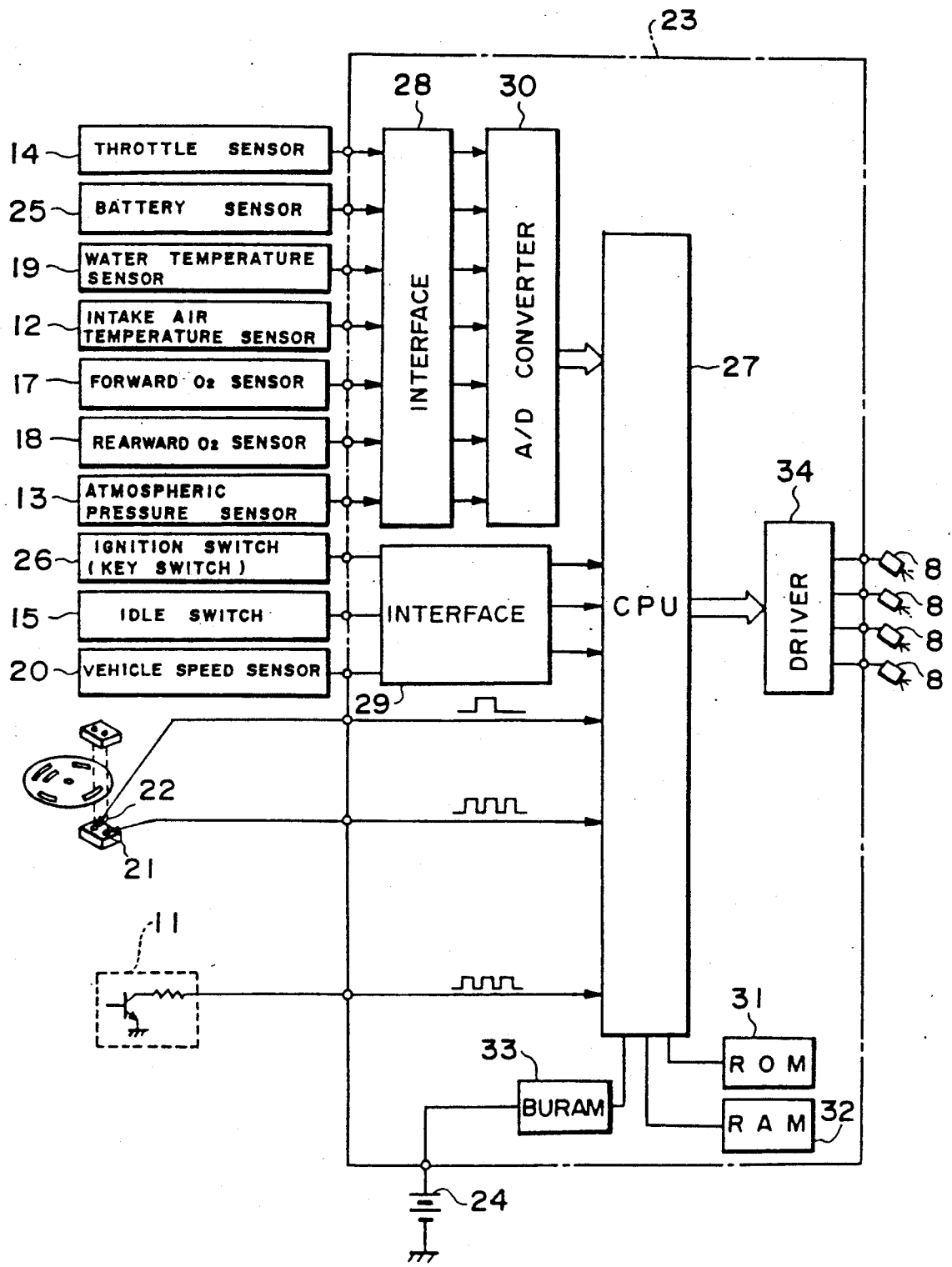

As other sensors, in addition to a water temperature sensor 19 for detecting the temperature of the cooling water for the engine and a vehicle speed sensor 20 (see FIG. 2) for detecting the vehicle speed, a crank angle sensor 21 for detecting the crank angle (which also serves as a revolutionary speed sensor for detecting the revolutionary speed of the engine) and a TDC sensor 22 for detecting the top dead center of a first cylinder (base cylinder) are also provided with the distributor as shown in FIG. 1(b) and FIG. 2.

Detection signals from these sensors 11–22 are inputted to an electronic control unit (ECU) 23.

Also inputted to the ECU 23 are a voltage signal from a battery sensor 25 for detecting the voltage of a battery 24 and a signal from an ignition switch (key switch) 26.

The hardware construction of the ECU 23 may be illustrated as shown in FIG. 2. The ECU 23 is equipped with a CPU 27 as its main element. The CPU 27 is fed with detection signals from the intake air temperature sensor 12, barometric sensor 13, throttle sensor 14, forward O₂ sensor 17, rearward O₂ sensor 18, coolant temperature sensor 19 and battery sensor 25 by way of an input interface 28 and/or an A/D converter 30. Detection signals from the idle sensor 15, vehicle speed sensor 20 and ignition switch 26 are also inputted through an input interface 29, while detection signals from the air flow sensor 11, crank angle sensor 21 and TDC sensor 22 are inputted directly to the input port.

Via bus lines, the CPU 27 performs transfer of data with an ROM 31 which serves to store program data and fixed-value data, an RAM 32 which is renewed and rewritten sequentially, and a battery backed-up RAM (BURAM) 33 which is backed up by the battery 24 to maintain its contents while the battery 24 is connected.

Incidentally, the RAM 32 is designed in such a way that data stored therein are erased and reset whenever the ignition switch 26 is turned off.

Let's now pay attention to the control of fuel injection (air/fuel ratio control). A fuel injection control signal which has been computed in a manner to be described subsequently is outputted from the CPU 27 via a driver 34, whereby the four solenoid valves 8 by way of example are successively actuated.

A function block diagram of such a fuel injection control (the control of the drive time of each solenoid valve) may be illustrated as shown in FIG. 1(b). Let's now make a discussion on the ECU 23 from the standpoint of its software. First of all, the ECU 23 is equipped with a basic energization time determination means 35 for determining the basic drive time $T_B$ for the solenoid valves 8. The basis energization time determination means 35 determines information on the intake air volume per revolution of the engine (Q/Ne) on the basis of information on an intake air quantity Q from the airflow sensor 11 and information on engine revolutionary speed Ne from the crank angle sensor 21 and then determines a basic drive time $T_B$ on the basis of the information.

There are also provided an air/fuel ratio upward correction means 36 for performing an upward correction of the air/fuel ratio in accordance with the revolutionary speed of the engine and the engine load (the above Q/Ne information contains engine load information) and an O₂ sensor feedback correction means 37 for conducting corrections of the O₂ sensors by setting a correction factor $K_{AF}$ upon performing the feedback control of the O₂ sensors. Either one of the air/fuel ratio upward correction means 36 and O₂ sensor feedback correction means 37 is selected by switching means 38,39 which are changed over in a mutually-interlocked manner.

Also provided are a coolant-temperature-dependent correction means 40 for setting a correction factor $K_{WT}$ in accordance with the temperature of the coolant for the engine, an intake-air-temperature-dependent correction means 41 for setting a correction factor $K_{AT}$ in accordance with the temperature of the air drawn, a barometric-pressure-dependent correction means 42 for setting a correction factor $K_{AP}$ in accordance with the barometric pressure, an accelerating-fuel-increment correction means 43 for setting a correction factor $K_{AC}$ for the increment of fuel quantity for acceleration, and a dead time correction means 44 for setting a dead time (ineffective time) $T_D$ for correcting the drive time in accordance with the voltage of the battery. During O₂ feedback control, the drive time TINJ of the solenoid valve 8 is eventually expressed by $T_B \times K_{WT} \times K_{AT} \times K_{AP} \times K_{AC} \times K_{IF} + T_D$ and the solenoid valve 8 is actuated for the drive time $T_{INJ}$.

Figure 5:
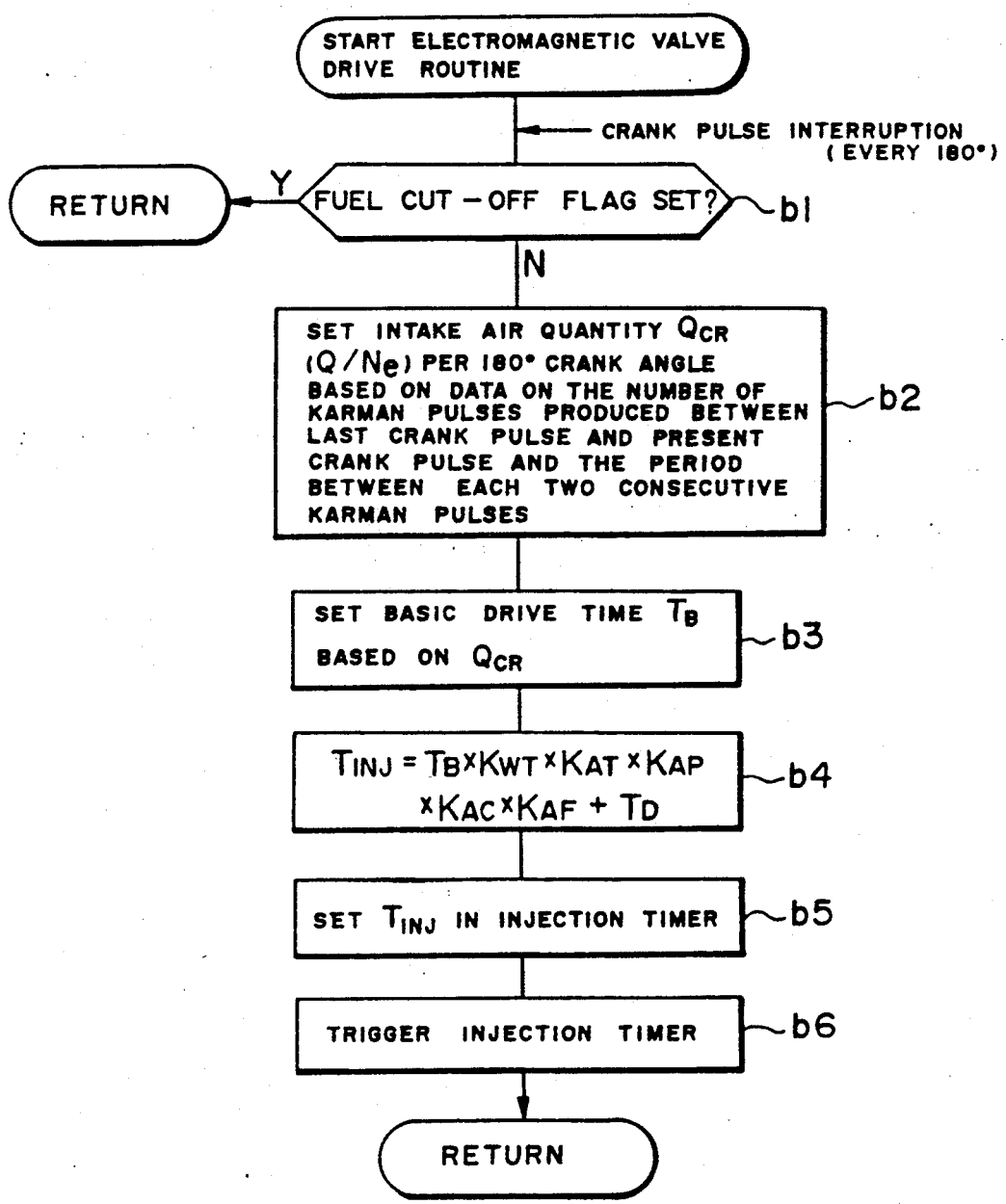

The procedure of such a control of the actuation of the solenoid valve may be illustrated like the flowchart of FIG. 5. The routine of the flow chart shown in FIG. 5 is performed by a crank pulse interruption which takes place every 180°. First of all, it is judged in step b1 whether a fuel cut-off flag has been set up or not. Where the fuel cut-off flag has been set up, no fuel injection is required and the routine returns. Otherwise, an intake air quantity QCR (Q/Ne) 7 per 180° crank angle is set up in step b2 on the basis of data on the number of Karman pulses produced between the last crank pulse and the present crank pulse and the period between the Karman pulses.

The routine then advances to step b3, where the basic drive time $T_B$ is set up in accordance with the QCR. The solenoid valve drive time TINJ is then determined in step b4 by computing it in accordance with $T_B \times K_{WT} \times K_{AT} \times K_{AP} \times K_{AC} \times K_{AF} \times T_D$. The TINJ is set in an injection timer in step b5 and is then triggered in step b6. By this trigger, the fuel is injected only for the time TINJ.

During the air/fuel ratio feedback control making use of the O$_2$ sensors, an output V1 from the forward O$_2$ sensor 17 is compared with a predetermined reference value V1c. Selected as the reference value V1c is an intermediate value between a high-level output (1 volt) and a low-level output (0 volt) of the forward O$_2$ sensor 17. The intermediate value functions as a so-called rich-/lean judgment voltage. The air-fuel mixture is rendered richer when V1c≦V1 but is rendered leaner when V1c≦V1.

Accordingly, the O$_2$ sensor feedback correction means 37 has, as depicted in FIG. 1(a), a first reference value setting means 45 for setting the first reference value V1c (for example, about 0.5 volt or so), a comparator means 46 for comparing the detection value V1 from the forward O$_2$ sensor 17 as the first air/fuel ration detection means with the predetermined reference value V1c, and a correction factor determination means 47 for determining the air/fuel ratio correction factor K$_{AF}$ in accordance with comparison results from the comparator means 46. As V1c, either the first reference value V1c or the second reference value V1c' is chosen. By the first reference value setting means 45A, comparator means 46 and correction factor determination means 47, there is constructed a air/fuel ratio control means 48 which controls the air/fuel ratio of the engine E on the basis of the comparison results between the detection value V1 from the forward O$_2$ sensor 17 and the predetermined reference value V1c.

The O$_2$ sensor feedback correction means 37 is equipped with a comparator means 53 for comparing a detection value V2 from the rearward O$_2$ sensor 18 as the second air/fuel detection means with a rearward O$_2$ reference value V2c from the reference value setting means 49A and also with an air/fuel ratio control correction means 49 for making a correction to the air/fuel ratio control by the above-described air/fuel ratio control means 48 on the basis of the comparison results from the comparator means 53. Namely, the air/fuel ratio control correction means 49 can correct the rich-/lean-judging first reference value V1c on the basis of a deviation ΔV of an output V2 of the rearward O$_2$ sensor 18, said deviation having been measured during the feedback control of the air/fuel ratio, from the reference value V2c for the rearward O$_2$ sensor as well as any of the response delay times DLYRL,DLYLR, proportional gains P$_{RL}$,P$_{LR}$ and integral gains I$_{RL}$,I$_{LR}$ on the basis of a deviation ΔV of an output V2 of the rearward O$_2$ sensor 18, said deviation having been measured during the feedback control of the air/fuel ratio, from the reference value V2c for the rearward O$_2$ sensor.

The O$_2$ sensor feedback correction means 37 is also equipped with a low-speed and low-load operation detection means for detecting a low-speed and low-load operation state (including small intake-air-quantity operation state, low-load operation state or idling state) of the engine E from the air flow sensor 11 or crank angle sensor 21 and also with a reference value shifting means 51 for shifting to a lean air/fuel ratio side the reference value V1c to be compared with the detection value V1 from the forward O$_2$ sensor 17. The reference value shifting means 51 is equipped not only with a second reference value setting means 45B for setting a second reference value V1c' smaller than the first reference value V1c (V1c' may be, for example, 0.3 volt when V1c is 0.5 volt) but also with a switching means 45C which is switched to feed the first reference value V1c as the reference value V1c from the first reference value setting means 45A to the comparator means 46 while no low-speed and low-load operation state is detected by the low-speed and low-load operation detection means 50 but which is switched to feed the second reference value V1c', said second reference value having been shifted to the lean side, as the reference value V1c from the second reference value setting means 45B to the comparator means 46.

The O$_2$ sensor feedback correction means 37 is also equipped with a means 52 for prohibiting any correction by the air/fuel ratio control correction means 49 in a low-speed and low-load operation state of the engine E.

Incidentally, the reference value V1c or V2c or the rich/lean-judging first reference voltage V1c corrected by an output V2 from the rearward O$_2$ sensor 18, the response delay times DLYRL,DLYLR, proportional gains P$_{RL}$,P$_{LR}$ and integral gains I$_{RL}$,I$_{LR}$ are stored in the BURAM 33.

A main routine for the air/fuel ratio control system, said main routine including the above-described shifting of the reference value, the determination of a correction factor, etc., will next be described with reference to FIG. 4.

Figure 4:
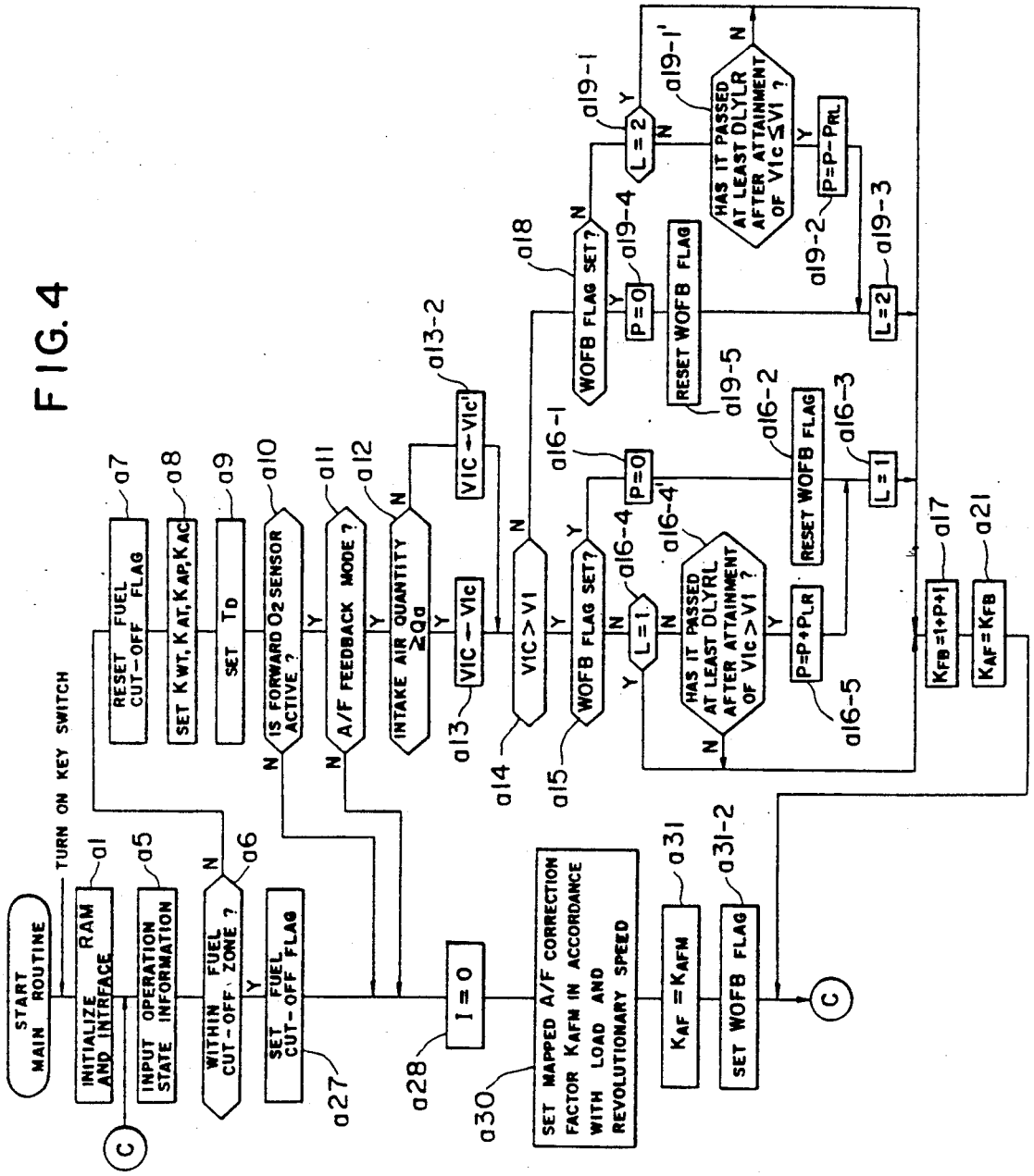

In this main flow, the routine is also started firstly as depicted in FIG. 4 when the key switch (ignition switch) is turned on. First of all, the RAM 32 and interfaces are initialized in step a1. Next, in step a5 (no steps a2–a4), information on the operation state is inputted and in the next step a6, it is judged whether the operation state is in a fuel cut-off zone or not. When it is not in the fuel cut-off zone, the fuel cut-off flag is reset in step a7, followed by setting of the correction factors K$_{WT}$, K$_{AT}$, K$_{AP}$ and K$_{AC}$ in step a8. The dead time T$_D$ is then set in step a9. These factors are set by the coolant-temperature-dependent correction means 40, intake-air-temperature-dependent correction means 41, barometric-pressure-dependent correction means 42, accelerating fuel-increment correction means 43 and dead time correction means 44, respectively.

In step a10 it is next judged from the output voltage value of the forward O$_2$ sensor 17 whether the sensor is in an active state or not.

If the forward O$_2$ sensor 17 is active, the routine advances to the next step a11 in which a judgment is made to determine whether it is in the air/fuel ratio (A/F) feedback mode or not.

If the operation is in the A/F feedback mode, it is judged in step a12 whether the quantity Q of intake air is not smaller than a small quantity Qa of intake air. If Q≧Qa, the first reference value V1c is set as the reference value V1c for comparison in step a13. If Q<Qa on the other hand, the second reference value V1c' (for example, 0.3 volt) is set as the reference value V1c in step a13-2. In this manner, the reference value to be compared with the detection value from the forward O$_2$ sensor 17 is changed in accordance with the quantity of intake air. Such operation is executed by the switching means 45C, low-speed and low-load operation detection means 50, etc.

Thereafter, in step a14, the output V1 of the forward O$_2$ sensor 17 and the rich/lean-judging voltage V1c are compared with each other. When V1c>V1, it is judged in step a15 whether WOFB flag has been set or not. Since WOFB flag is in a set state at the time point immediately after the A/F feedback zone has been entered, the routine takes the YES route, the proportional gain P is changed to 0 in step a16-1, WOFB flag is reset in step a16-2, and Flag L is changed to 1 in step a16-3.

After step a16-3, the feedback correction factor $K_{FB}$ is determined as $1+P+I$ in step a17 and this value $K_{FB}$ is inputted to an address $K_{AF}$ in step a21. At the beginning, the proportional gain $P=0$ and the integral factor $I=0$. The routine therefore starts with $K_{FB}=1$ and then returns to step a5.

After returning again to step a15, the NO route is taken this time since WOFB flag has been reset in step a16-2. It is then judged in step a16-4 whether Flag L is 1 or not. Since Flag L has been changed to 1 in this case in step a16-3, the YES route is taken to perform the processing of step a17.

Figure 6:
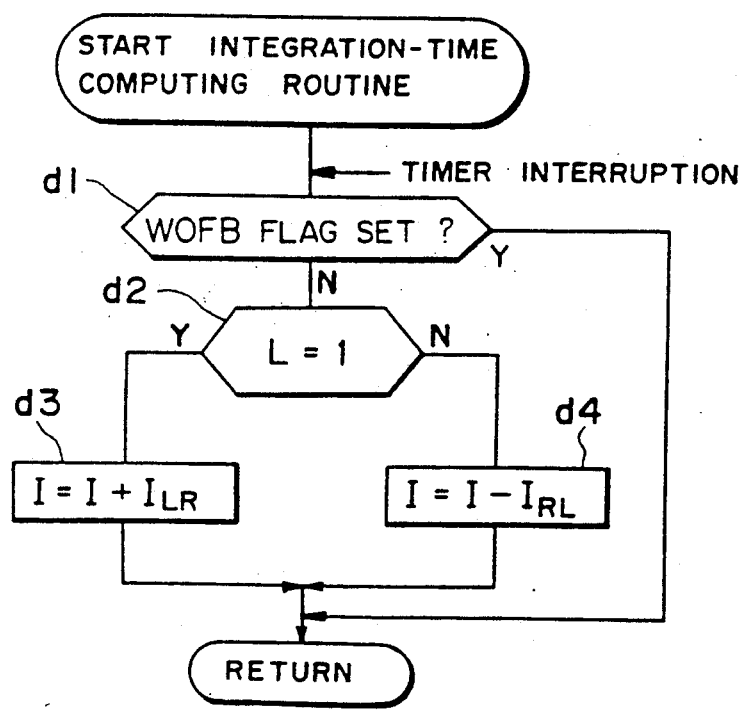

Incidentally, a routine for the calculation of an integral time for the integral factor I can be illustrated as such a flow chart as shown in FIG. 6. In this routine, it is judged in step d1 whether WOFB flag has been set or not upon every time interruption. When WOFB has been reset (in the A/F feedback mode), it is judged in step d2 whether L is 1 or not. If $L=1$, the sum of I and $I_{LR}$ (enriching integral factor) is set as a new I. If L is not 1 in step d2 in contrast, the difference obtained by subtracting $I_{RL}$ (leaning integral factor) from I is set newly as I. Accordingly, $I_{LR}$ is added upon every time interruption while $L=1$ but $I_{RL}$ is subtracted upon every time interruption while $L\neq$(while $L=2$). The feedback correction factor $K_{FB}$ increases while $I_{LR}$ is added, so that enrichment is promoted. While $I_{LR}$ is subtracted, the feedback correction factor $K_{FB}$ becomes smaller so that leaning is promoted.

Since $L=1$ in this case, $I_{LR}$ is added at every time interruption and the feedback correction factor $K_{FB}$ becomes greater. The enrichment is therefore promoted.

When V1c becomes equal to or smaller than V1 ($V1c \geq V1$) as a result of enrichment in the above-described manner, the NO route is taken in step a14, and it is judged in step a18 whether WOFB flag has been set or not. When the operation is still in the A/F feedback mode, WOFB flag is still in the reset state. The NO route is therefore followed after step a18, and in step a19-1, a judgment is made to determine if Flag L is 2. Since $L=1$ immediately after the switching, the NO route is taken in step a19-1. In step a19-1', subsequent to the attainment of $V1c \geq V1$, it is judged whether the delay time DLYLR has lapsed. While the delay time DLYLR has not lapsed the NO route is taken to perform the processing of step a17. After the delay time DLYLR has been lapsed, the YES route is taken and the proportional gain $P_{RL}$ for leanness is subtracted from the proportional gain P. The difference is then set as P. After changing L to 2 ($L=2$) in step a19-3, the feedback correction factor $K_{FB}$ is determined as $1+P+I$ in step a17. This value $K_{FB}$ is inputted to the address $K_{AF}$ in step a21. As a result, the feedback correction factor $K_{FB}$ is decreased by the proportional gain $P_{RL}$ for leanness from its maximum value.

Thereafter, the routine returns to step a5 in the same manner as described above.

When the routine has returned again to step a19-1 via step a18, the YES route is taken this time because L has been changed to 2 in step a19-3. The processing of step a17 is therefore applied.

Since $L=2$ in this case, at every timer interruption, the NO route is taken in step d2 of FIG. 6 and $I_{RL}$ is subtracted in step d4 of the same figure, and the feedback correction factor $K_{FB}$ becomes smaller. The leanness is therefore promoted.

When V1c becomes greater than V1 ($V1c > V1$) as a result of leaning in the above-described manner, the YES route is taken in step a14, and it is judged in step a15 whether WOFB flag has been set or not. When the operation is still in the A/F feedback mode, WOFB flag is still in the reset state. The NO route is therefore followed after step a15, and in step a16-4, a judgment is made to determine whether Flag L is 1 or not. Since $L=2$ immediately after the switching, the NO route is taken in step a16-4. After attainment of $V1c > V1$ in step a16-4', it is judged whether the delay time DLYRL has lapsed or not. While the delay time DLYRL has not lapsed, the NO route is taken to perform the processing of step a17. After the delay time DLYRL has lapsed, the YES route is taken and the proportional gain $P_{LR}$ for enrichment is added to the proportional gain P in step a16-5 so as to use the sum as P. After changing L to 1 ($L=1$) in step a16-3, the feedback correction factor $K_{FB}$ is determined as $1+P+I$ in step a17. This value $K_{FB}$ is then inputted to the address $K_{AF}$ in step a21. As a consequence, the feedback correction factor $K_{FB}$ is increased by the proportional gain $P_{LR}$ for enrichment from its minimum value.

Figure 12A:
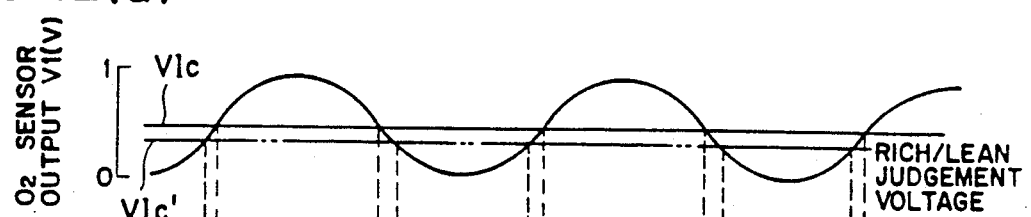
Figure 12B:
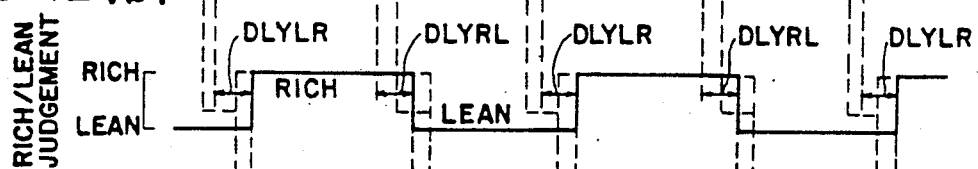
Figure 12C:
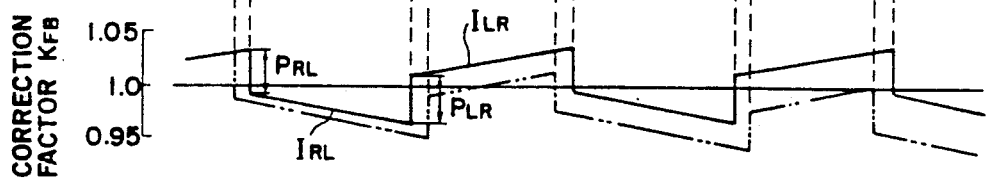

By repeating the above processing thereafter, the feedback correction factor $K_{FB}$ is varied as shown in FIG. 12(c) so that the desired air/fuel ratio control is performed in the A/F feedback mode.

Incidentally, FIG. 12(a) is a waveform diagram of the output of the forward $O_2$ sensor, while FIG. 12(b) is a waveform diagram for the rich/lean judgment. The delay times DLYRL,DLYLR are, as illustrated in FIG. 12(b), times corresponding to the delays until a rich/lean judgment is performed when the output of the $O_2$ sensor has crossed the rich/lean judgment voltage V1c upwardly or downwardly as illustrated in FIG. 12(a).

When $V1c \leq V1$ immediately after entering the A/F feedback zone, the YES route is also followed in step a18 since WOFB flag is in a set state at the time point immediately after the entrance, the proportional gain P is changed to 0 in step a19-4, WOFB flag is reset in step a19-5, and Flag L is changed to 2 in step a19-3. After step a19-3, the feedback correction factor $K_{FB}$ is determined as $1+P+I$ in step a17 and this value $K_{FB}$ is inputted to the address $K_{AF}$ in step a21. Here again, the proportional gain and integral factor I are both 0 ($P=0$, $I=0$) at the beginning, and the routine also starts from $K_{FB}=1$.

As has been described above, it is the comparator means 46 and correction factor determination means 47 in the $O_2$ sensor feedback correction means 37 that perform the comparison between V1c and V1 and determine the correction factor $K_{AF}$ on the basis of results of the comparison.

In this embodiment, these delay times DLYRL, DLYLR, proportional gains $P_{RL},P_{LR}$, integral gains $I_{RL},I_{LR}$ and first reference value V1c are variable as will be described subsequently.

When the operation is found to be in the fuel cut-off zone in step a6 subsequent to step a5, the fuel cut-off flag is set in step a27, the integral factor I is changed to 0 in step a28, and the mapped A/F correction factor $K_{AFM}$ is set in accordance with the load and revolutionary speed of the engine in step a30. The mapped A/F correction factor $K_{AFM}$ is inputted to the address $K_{AF}$ in step a31, and after setting WOFB flag in step a31-2, the routine returns to step a5 to perform the subsequent processings.

When the answer is "NO" in step a10 or a11, it is impossible to perform the A/F feedback control. The routine therefore returns to step a5 via steps a28, a30, a31 and a31-2.

The above routine is performed repeatedly as described above, so that the factors $K_{WT}, K_{AT}, K_{AP}, K_{AC}, K_{AF}$ and the time $T_D$ are set in accordance with the state of the engine. By conducting the solenoid valve drive routine depicted in FIG. 5 by using these values, each solenoid valve 8 is actuated to inject a desired quantity of fuel. In this manner, the desired air/fuel ratio control is effected.

In an operation zones other than the small intake-air-quantity operation zone, the reference value to be compared with the detection value V1 from the forward $O_2$ sensor 17 is set as V1c (about 0.5 volt or so). In the small intake-air-quantity operation zone, the reference value to be compared with the detection value V1 from the forward $O_2$ sensor is set as V1c' (about 0.3 volt or so), whereby the reference value for the control of the air/fuel ratio is shifted to a lean air/fuel ratio side [see the dashed lines in FIGS. 12(a) through 12(c)].

A description will next be made of a method for correcting the response delay times DLYRL, DLYLR, proportional gains $P_{RL}, P_{LR}$, integral gains $I_{RL}, I_{LR}$ and rich/lean-judging reference value V1c on the basis of the output V2 of the rearward $O_2$ sensor and the reference value V2c for the rearward $O_2$ sensor.

Figure 7:
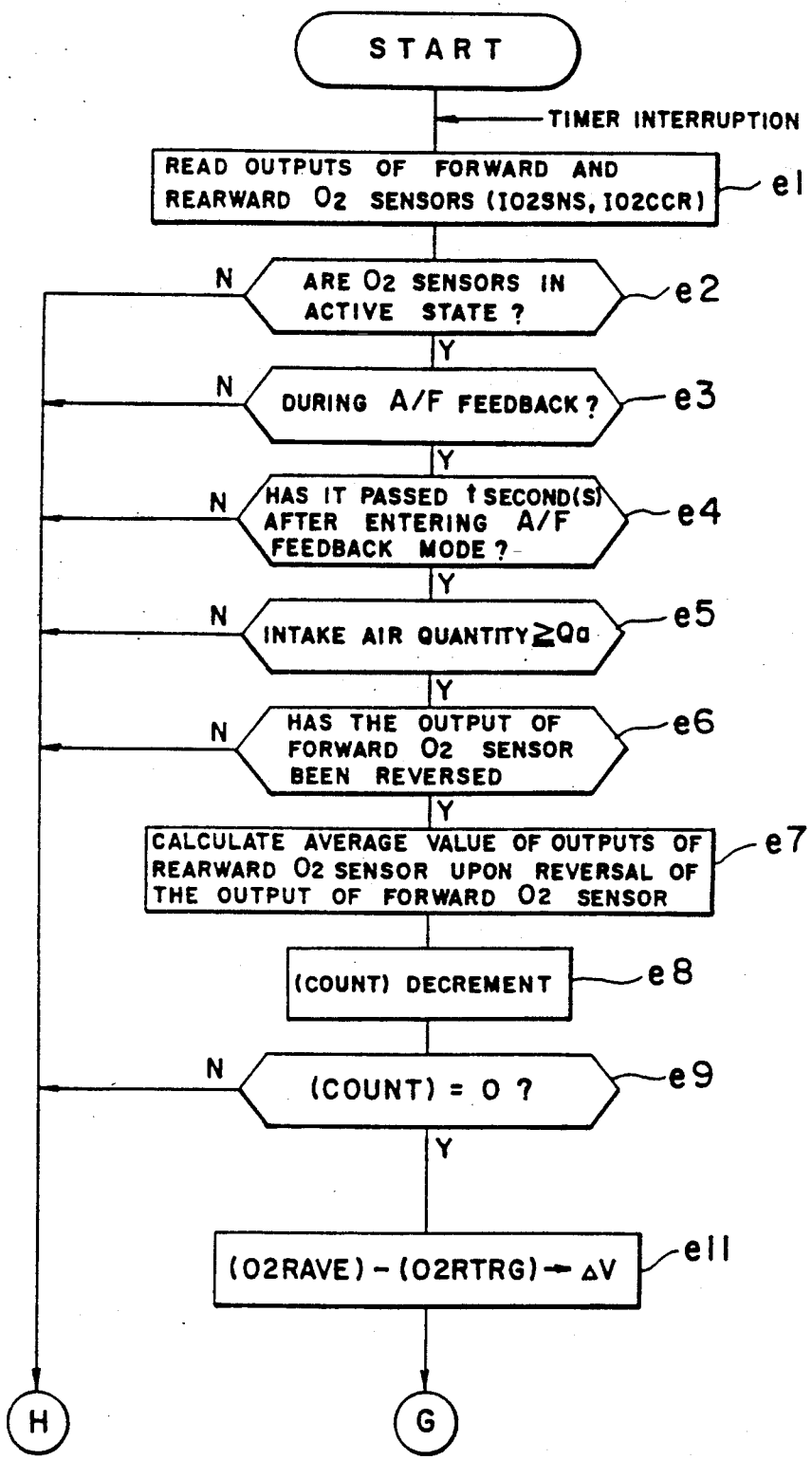

As shown in FIG. 7, the outputs IO2SNS (V1) and IO2CCR (V2) of the forward and rearward $O_2$ sensors 17,18 are read in first of all in step e1. As the timing of their reading, they may be read in, for example, every 5 msec or every 10 msec. In step e2, it is then judged from the output voltage values of the forward and rearward $O_2$ sensors 17,18 whether they are in an active state or not. For the above judgment, it should be noted that separate reference voltage values can be set for the forward $O_2$ sensor 17 and rearward $O_2$ sensor 18.

If both $O_2$ sensors 17,18 are in an active state, it is judged in step e3 whether the operation is in the air/fuel ratio feedback or not. If the answer is "YES", the routine advances to step e4 where a judgment is made to determine whether a predetermined period of time has lapsed after the entrance to the air/fuel ratio feedback mode. If the answer is "YES", it is judged in step e5 whether the quantity Q of intake air is not smaller than the low quantity Qa. If $Q \geq Qa$ in step e5, the response delay times DLYRL, DLYLR, proportional gains $P_{RL}, P_{LR}$, integral gains $L_{RL}, L_{LR}$ and rich/lean-judging reference value V1c are corrected on the basis of the output V2 from the rearward $O_2$ sensor and its reference value V2c. Otherwise, the routine returns directly so that the above corrections are not effected. Accordingly, the above corrections are prohibited in the low-speed and low-load operation state. The air/fuel ratio control prohibiting means 52 has such function.

As has been described above, the above corrections are performed when the answer is "YES" in step e5. First, it is judged in step e6 whether the output of the forward $O_2$ sensor 17 has been reversed or not. When the answer is "NO" in step e6, the routine returns. Otherwise, the average output value of the rearward $O_2$ sensor 18 is renewed on the basis of the short-term output value IO2CCR of the rearward $O_2$ sensor 18 at the time of reversal of the output of the forward $O_2$ sensor and the average output value of the rearward $O_2$ sensor 18 already in storage. Namely, a new average output value O2RAVE of the rearward $O_2$ sensor 18, which is expressed by the left-hand member of the following equation, is determined as follows:

$$O2RAVE = K1(IO2CCR) + (1-K_1)(O2RAVE)$$

Incidentally, O2RAVE in the right-hand member of the above formula indicates the last datum of the average output value of the rearward $O_2$ sensor 18, which had replaced the previous one in step e7 of the last performance of the time interruption routine and has been stored in the RAM.

Here, K1 is a factor set as a datum in the ROM.

In addition, the contents of the counter COUNT are reduced by 1 in step e8. Here, the initial value of the counter is set by the data of the ROM and a desired value from 1 to 255 may be set by way of example. This initial value was set in the counter in step a1 of the main routine shown in FIG. 4 when the key switch was turned on.

In the next step e9, it is judged whether the number of the counter has been counted down to 0. If the answer is "NO", the routine returns. When the answer becomes "YES" (namely, the smoothing processing of output data of the rearward $O_2$ sensor 18 has been performed fully), the routine advances to step e11 where from a target output voltage value O2RTRG (which corresponds to V2c) of the rearward $O_2$ sensor) and the average output value O2RAVE of the rearward $O_2$ sensor 18 at the time of rich/lean reversal of the forward $O_2$ sensor 17, the deviation $\Delta V$ of the latter value from the former is determined. By the way, the initial value upon turning on the key switch is set equal to the target output value, namely, O2RTRG.

When the deviation $\Delta V$ has been determined as described above, the characteristic values for the air/fuel ratio feedback control, namely, the response delay times, integral gains, proportional gains and first reference value V1c are corrected by using $\Delta V$.

Since variations of the output V2 of the rearward $O_2$ sensor 18 are slow during the air/fuel ratio feedback control, it is not preferable to use the output V2 directly for the air/fuel ratio feedback control. The output V2 is however produced with substantially the same delay when the air/fuel ratio changes from the lean side to the rich side and vice versa. It is hence useful for such corrections of characteristic values for the air/fuel ratio feedback control as described above.

Figure 8:
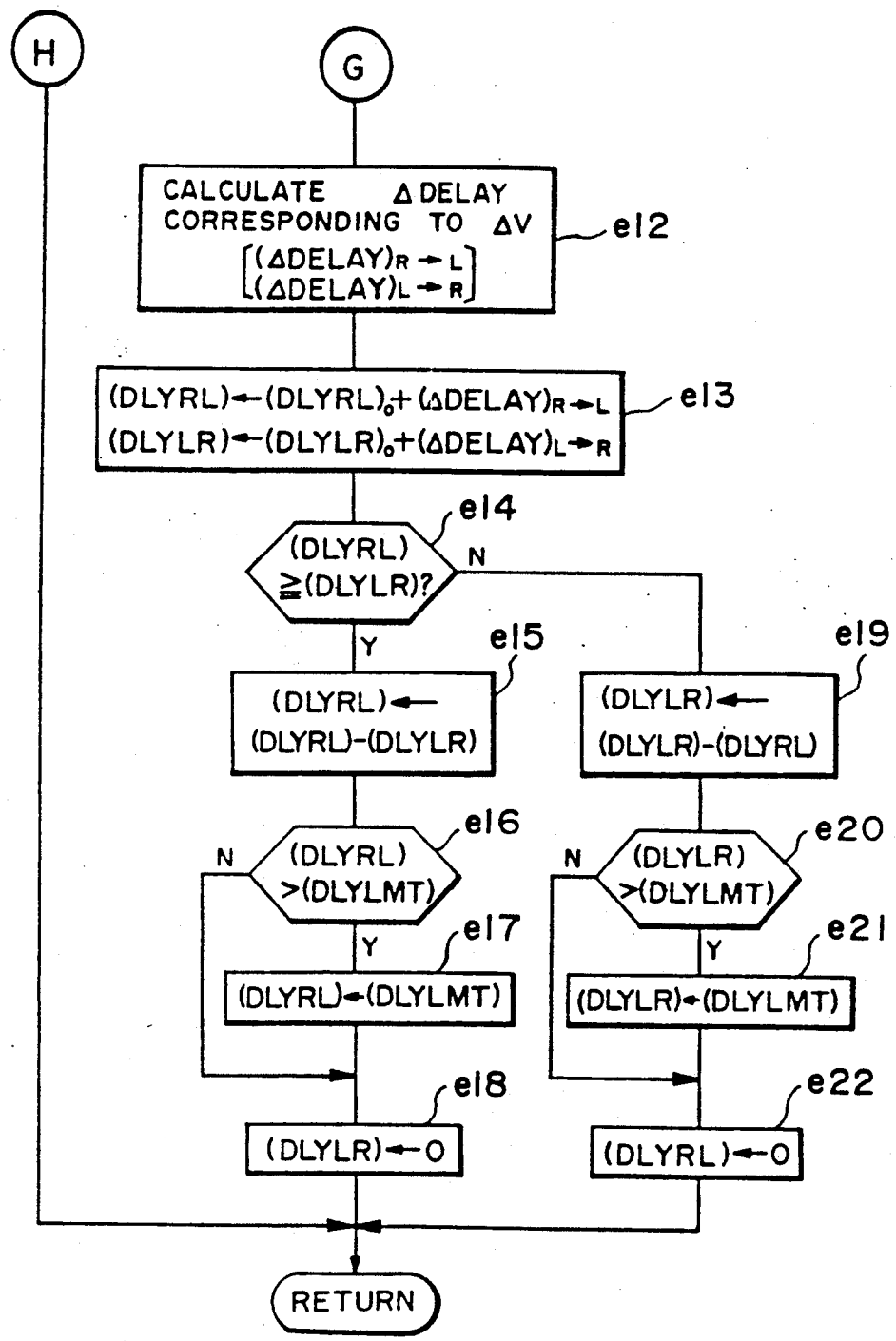

The corrections of the response delay times DLYRL, RLYLR are described first of all. As shown in FIG. 8, $\Delta$DELAY corresponding to $\Delta V$ obtained in step e11 of FIG. 7 is determined first of all in step e12.

Figure 13A:
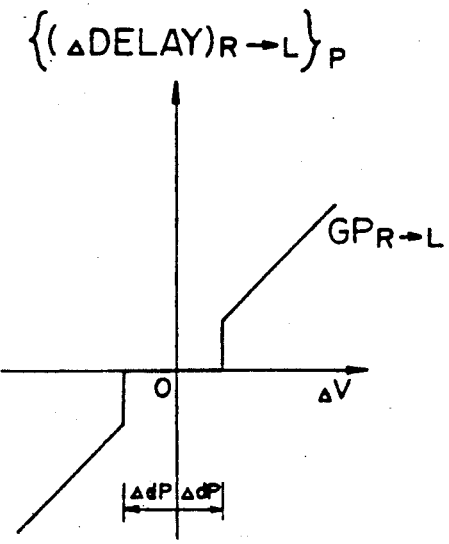
FIGS. 13(a) and 13(b) and FIGS. 14(a) and 14(b) are respectively graphs for describing a correction value for a response delay time.
Figure 13B:
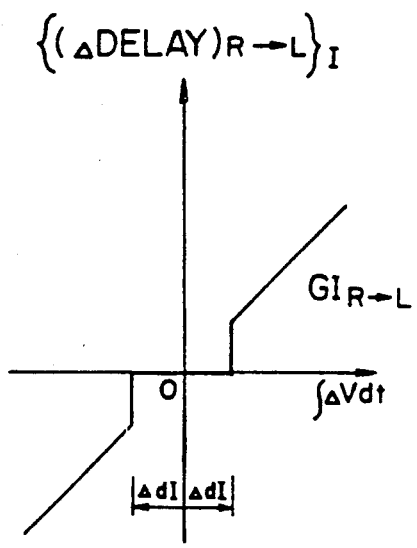
Figure 14A:
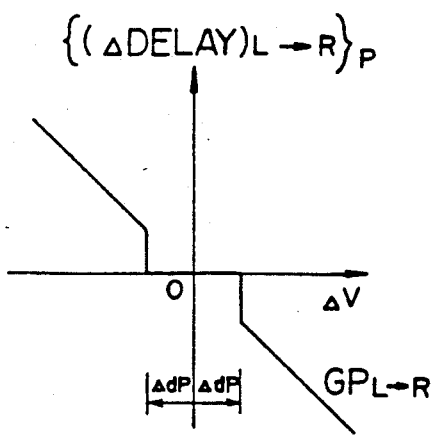
Figure 14B:
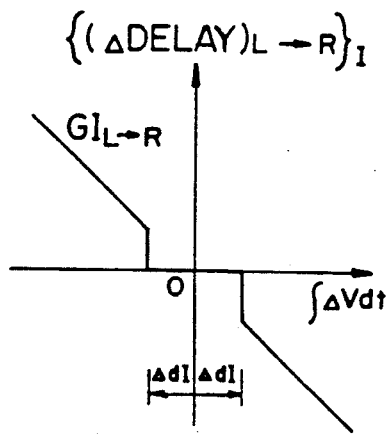

By the way, there are two kinds of delays as $\Delta$DELAY, one being a delay that takes place when the air/fuel ratio changes from the rich side to the lean side and the other being a delay that occurs when the air/fuel ratio changes from the lean side to the rich side. Correction characteristics for the former delay may be illustrated as shown in FIGS. 13(a) and 13(b), while those for the latter delay may be depicted as shown in FIGS. 14(a) and 14(b). Namely, $\Delta$DELAY is given as the sum of $(\Delta DELAY)_p$ based on a short-term value of $\Delta V$ and $(\Delta DELAY)_I$ based on an integrated value of $\Delta V$. It may hence be expressed as follows:

$$(\Delta DELAY)_{R \to L} = \{(\Delta DELAY)_{R \to L}\}_I + \{(\Delta DELAY)_{R \to L}\}_P$$

$$(\Delta DELAY)_{L \to R} = \{(\Delta DELAY)_{L \to R}\}_I + \{(\Delta DELAY)_{L \to R}\}_P$$

Inclinations GP,GI shown in these FI 13(b) and FIGS. 14(a) and 14(b) as well as dead zones ΔdP,ΔdI are set in the ROM data.

After determination of ΔDELAY in the above manner, these ΔDELAYs are added respectively to reference values (DLYRL)$_o$ and (DLYLR)$_o$ of DLYRL and DLYLR in step e13, thereby determining new DLTRL and DLYLR.

In the next step e14, it is judged whether DLYRL is either equal to or greater than DLYLR (DLYRL≧ DLYLR). If the answer is "YES", result obtained by subtracting DLYLR from DLYRL are set as new DLYRL in step e15. In the next step e16, it is judged whether DLYRL is greater than DLYLMT (delay limiting value: set by the ROM data) or not. While DLYRL has not reached this limiting value, step e17 is jumped over, DLYLR is changed to 0 in step e18, and the routine returns. When DLYRL reaches the limiting value, the limiting value is set as DLYRL in step e17 and the processing of step e18 is then applied.

If DLYRL<DLYLR in step e14, results obtained by subtracting DLYRL from DLYLR are set as new DLYLR in step e19. In the next step e20, it is judged whether DLYLR is greater than DLYLMT (delay limiting value: set by the ROM data) or not. While DLYLR has not reached this limiting value, step e21 is jumped over, DLYRL is changed to 0 in step e22, and the routine returns. When DLYLR reaches the limiting value, the limiting value is set as DLYLR in step e21 and the processing of step e22 is then applied.

The delay limiting values compared in steps e16,e20 respectively may be the same or different.

Although DLYRL and DLYLR are both backed up by a battery, their initial values may be set, for example, at 0 when the battery is disconnected.

When DLYRL and DLYLR are corrected on the basis of the output of the rearward O$_2$ sensor 18 to make the air/fuel ratio richer as described above, DLYLR is added as shown in FIGS. 20(a) through 20(c). For rendering the air/fuel ratio leaner, DLYRL is added as illustrated in FIGS. 21(a) through 21(c).

As has been described above, the output V2 of the rearward O$_2$ sensor 18 is measured during the air/fuel ratio feedback control at constant time intervals (or whenever the output V1 of the forward O$_2$ sensor 17 crosses the first reference value V1c) and the correction of the response delay time is effected to make its moving average equal to V2c.

Figure 9:
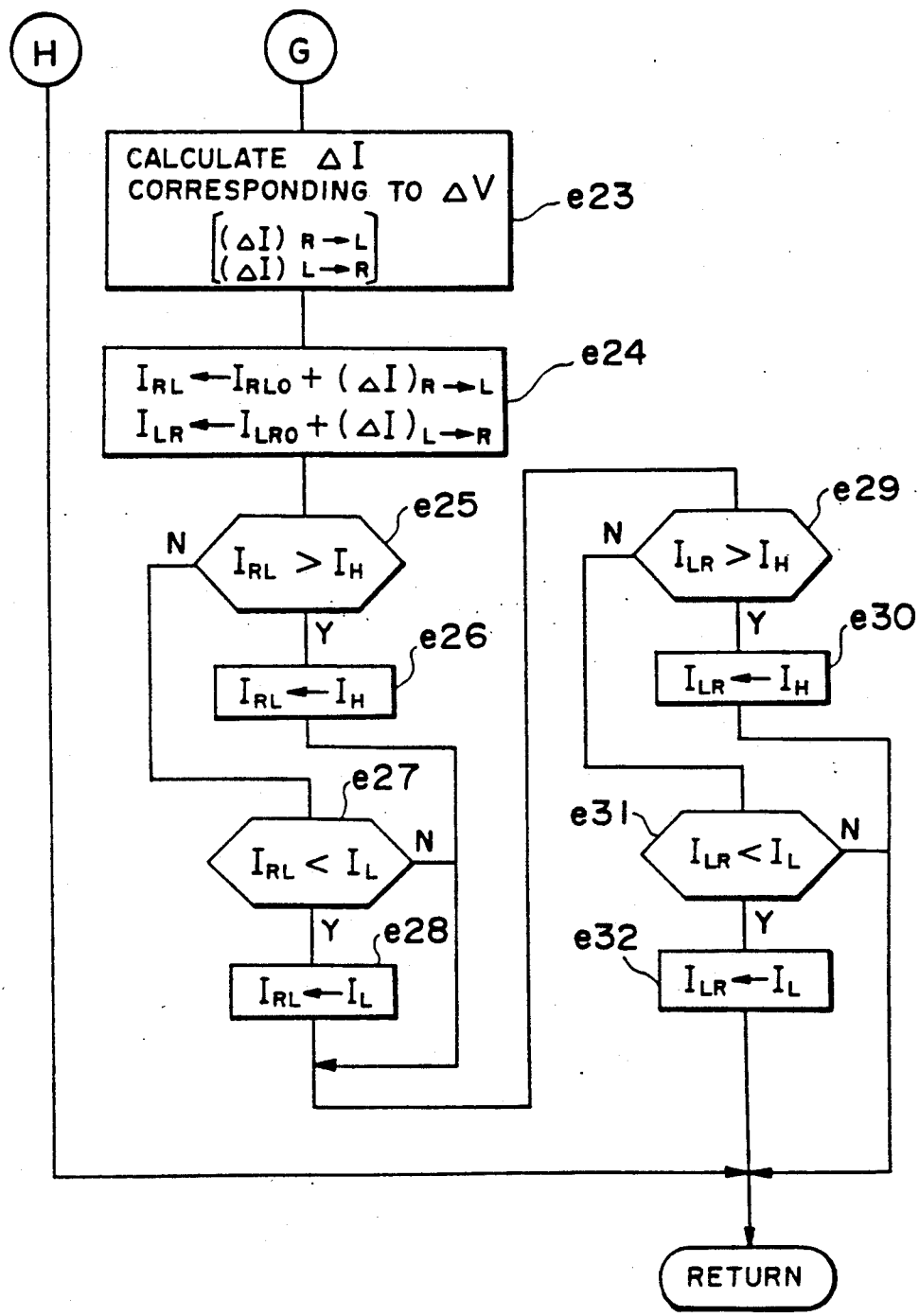

A description will next be made of the corrections of the integral gains I$_{RL}$,I$_{LR}$ for the air/fuel ratio feedback control. As illustrated in FIG. 9, ΔI corresponding to ΔV obtained in step e11 of FIG. 7 is determined first of all in step e23.

Figure 15A:
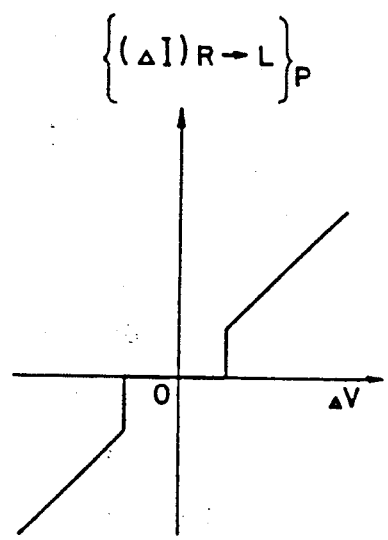
FIGS. 15(a) and 15(b) and FIGS. 16(a) and 16(b) are respectively graphs for illustrating a correction value for an integral gain which is for the air/fuel ratio feedback control.
Figure 15B:
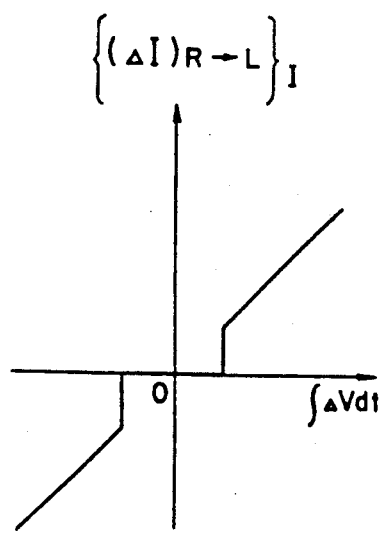
Figure 16A:
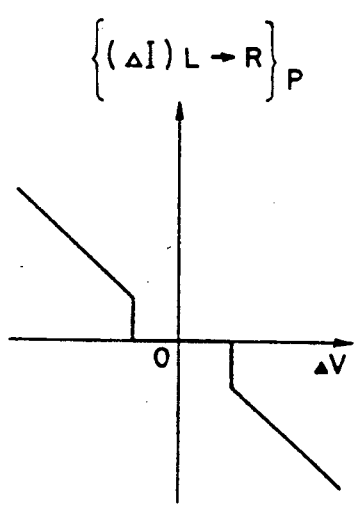
Figure 16B:
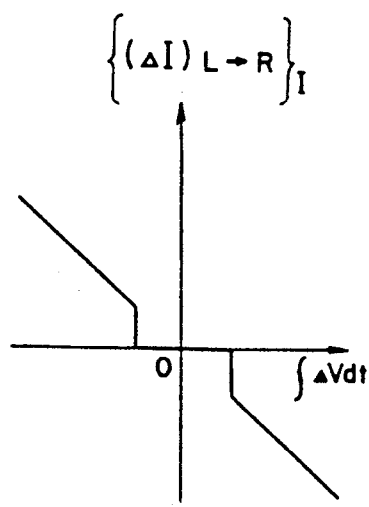

By the way, there are two kinds of integral gains as ΔI, one being an integral gain for the change of the air/fuel ratio from the rich side to the lean side and the other being an integral gain for the change of the air/fuel ratio from the lean side to the rich side. Correction characteristics for the former integral gain may be illustrated as shown in FIGS. 15(a) and 15(b), while those for the latter integral gain may be depicted as shown in FIGS. 16(a) and 16(b). Namely, ΔI is given as the sum of $\{\Delta I\}_P$ based on a short-term value of ΔV and $\{\Delta I\}_I$ based on an integral value of ΔV. It may hence be expressed as follows:

$(\Delta I)_{R \to L} = \{(\Delta I)R \to L\}_I + \{(\Delta I)R \to L\}_P$
$(\Delta I)_{L \to R} = \{(\Delta I)_{L \to R}\}_I + \{(\Delta I)_{L \to R}\}_P$ Functional relations (inclinations and dead zones) shown in these FIGS. 15(a) and 15(b) and FIGS. 16(a) and 16(b) are set in the ROM data.

After determination of ΔIs in the above manner, these ΔIs are added respectively to reference values I$_{RLo}$ and I$_{LRo}$ of I$_{RL}$ and I$_{LR}$ in step e24, thereby determining new I$_{RL}$ an I$_{LR}$.

In the next step e25, it is judged whether I$_{RL}$ is greater than I$_H$(upper limit: this value is set in the ROM data; I$_{RL}$>IH). If the answer is "NO", it is judged in step e27 whether I$_{RL}$ is smaller than I$_L$ (lower limit: this value is set in the ROM data; I$_{RL}$<I$_L$).

If the answer is "YES" in step e25, I$_H$ is set as I$_{RL}$ in step e26. If the answer is "YES" in step e27, IL is set as I$_{RL}$ in step e28.

If the answer is "NO" in step e27 or after the processings of steps e26,e28, it is judged in the next step e29 whether I$_{LR}$ is greater than I$_H$(upper limit: this value is set in the ROM data). If the answer is "NO", it is judged in step e31 whether I$_{LR}$ is smaller than I$_L$ (lower limit: this value is set in the ROM data; I$_{LR}$>I$_L$).

If the answer is "YES" in step e29, I$_H$ is set as I$_{LR}$ in step e30. Further, if the answer is "YES" in step e31, I$_L$ is set as I$_{LR}$ in step e32 and the routine then returns.

Incidentally, the individual upper limits compared in steps e25,e29 may be the same or different. Further, the lower limits compared in steps e27,e31 may also be the same or different.

Further, the integral gains I$_{RL}$ and I$_{LR}$ are both backed up by the battery.

When I$_{RL}$ and I$_{LR}$ are corrected on the basis of the output V2 of the rearward O$_2$ sensor 18 and the air/fuel ratio is rendered richer, I$_{RL}$ is rendered smaller and at the same time, I$_{LR}$ is rendered greater as illustrated in FIGS. 22(a) through 22(c). For rendering the air/fuel ratio leaner, I$_{RL}$ is rendered greater and at the same time, I$_{LR}$ is rendered smaller as illustrated in FIGS. 23(a) through 23(c).

As has been described above, the output V2 of the rearward O$_2$ sensor 18 is measured during the air/fuel ratio feedback control at constant time intervals (or whenever the output V1 of the forward O$_2$ sensor 17 crosses the first reference value V1c) and the correction of the integral gain is effected to make its moving average equal to V2c.

Figure 10:
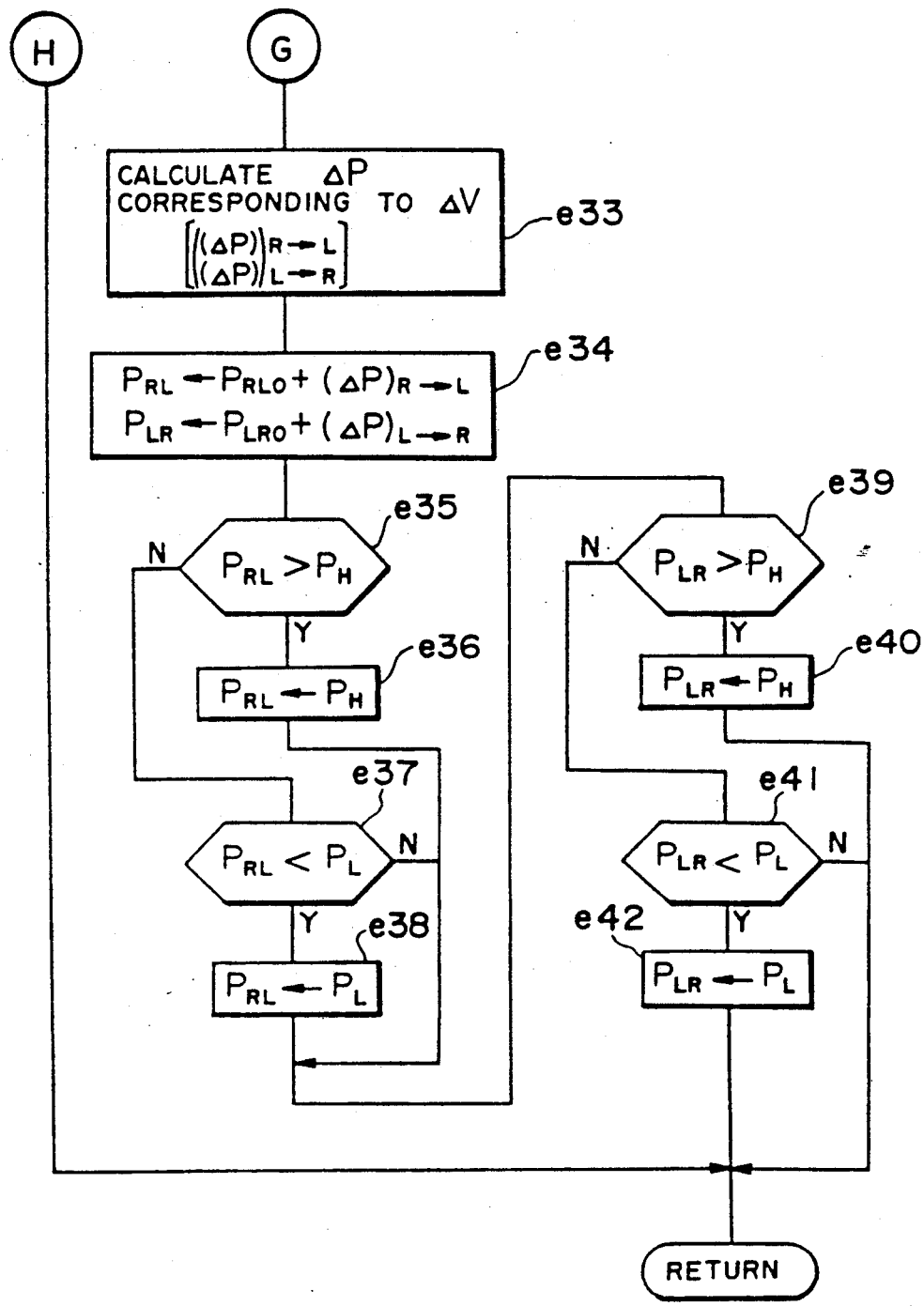

The corrections of the proportional gains P$_{RL}$,P$_{LR}$ for the air/fuel ratio feed back control will next be described. As illustrated in FIG. 10, ΔP corresponding to ΔV obtained in step e11 of FIG. 7 is determined in step e33.

Figure 17A:
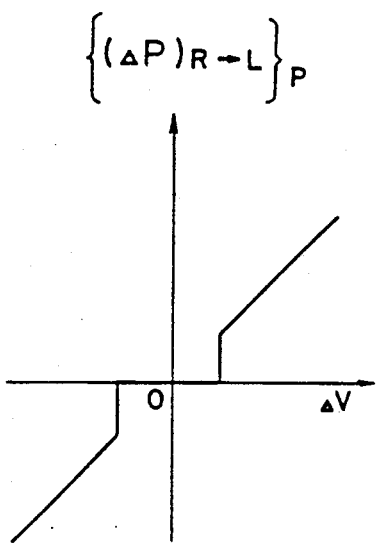
FIGS. 17(a) and 17(b) and FIGS. 18(a) and 18(b) are respectively graphs for illustrating a correction value for a proportional gain which is for the air/fuel ratio feedback control.
Figure 17B:
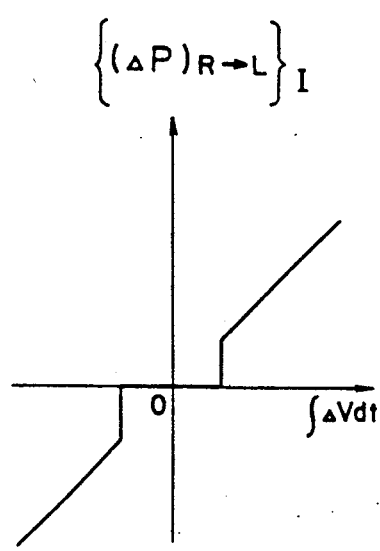
Figure 18A:
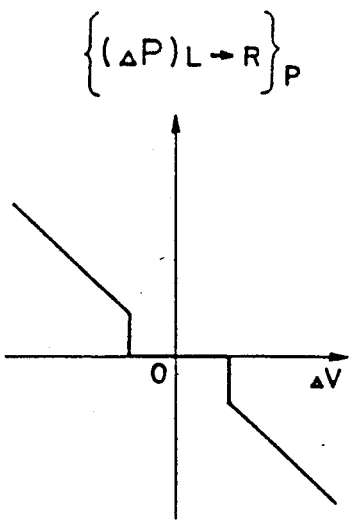
Figure 18B:
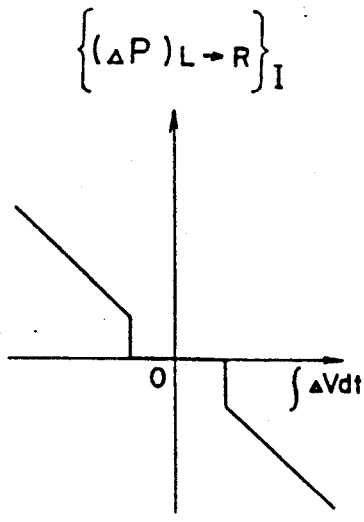

By the way, there are two kinds of proportional gains as ΔP, one being a proportional gain for the change of the air/fuel ratio from the rich side to the lean side and the other being a proportional gain for the change of the air/fuel ratio from the lean side to the rich side. Correction characteristics for the former proportional gain may be illustrated as shown in FIGS. 17(a) and 17(b), while those for the latter proportional gain may be depicted as shown in FIGS. 18(a) and 18(b). Namely, ΔP is given as the sum of $\{\Delta P\}_P$ based on a short-term value of ΔV and $\{\Delta P\}_I$ based on an integral value of ΔV. It may hence be expressed as follows:

$(\Delta P)_{R \to L} = \{(\Delta P)_{R \to L}\}_I + \{(\Delta P)_{R \to L}\}_P$
$\{(\Delta P)_{L \to R} = \}(\Delta P)_{L \to R})_I + \{(\Delta P)_{L \to R}\}_P$ Functional relations (inclinations and dead zones) shown in these FIGS. 17(a) and 17(b) and FIGS. 18(a) and 18(b) are set in the ROM data.

After determination of ΔPs in the above manner, these ΔPs are added respectively to reference values $P_{RLo}$ and $P_{LRo}$ of $P_{RL}$ and $P_{LR}$ in step e34, thereby determining new $P_{RL}$ and $P_{LR}$.

In the next step e35, it is judged whether $P_{RL}$ is greater than $P_H$ (upper limit: this value is set in the ROM data). If the answer is "NO", it is judged in step e37 whether $P_{RL}$ is smaller than $P_L$ (lower limit: this value is set in the ROM data; $P_{RL} < P_L$).

If the answer is "YES" in step e35, $P_H$ is set as $P_{RL}$ in step e36. If the answer is "YES" in step e37, $P_L$ is set as $P_{RL}$ in step e38.

If the answer is "NO" in step e37 or after the processings of steps e36,e38, it is judged in the next step e39 whether $P_{LR}$ is greater than $P_H$ (upper limit: this value is set in the ROM data; $P_{LR} > P_H$). If the answer is "NO", it is judged in step e41 whether $P_{LR}$ is smaller than $P_L$ (lower limit: this value is set in the TOM data; $P_{LR} < P_L$), If the answer is "YES" in step e39, $P_H$ is set as $P_{LR}$ in step e40. Further, if the answer is "YES" in step e41, $P_L$ is set as $P_{LR}$ in step e42 and the routine then returns.

Incidentally, the individual upper limits compared in steps e35,e39 may be the same or different. Further, the lower limits compared in steps e37,e41 may also be the same or different.

Further, the proportional gains $P_{RL}$ and $P_{LR}$ are both backed up by the battery.

When $P_{RL}$ and $P_{LR}$ are corrected on the basis of the output V2 of the rearward $O_2$ sensor and the air/fuel ratio is rendered richer, $P_{RL}$ is rendered smaller and at the same time, $P_{LR}$ is rendered greater as illustrated in FIGS. 24(a) through 24(c). For rendering the air/fuel ratio leaner, $P_{RL}$ is rendered greater and at the same time, $P_{LR}$ is rendered smaller as illustrated in FIGS. 25(a) through 25(c).

As has been described above, the output V2 of the rearward $O_2$ sensor 18 is measured during the air/fuel ratio feedback control at constant time intervals (or whenever the output V1 of the forward $O_2$ sensor 17 crosses the first reference value V1c) and the correction of the proportional gain is effected to make its moving average equal to V2c.

Figure 11:
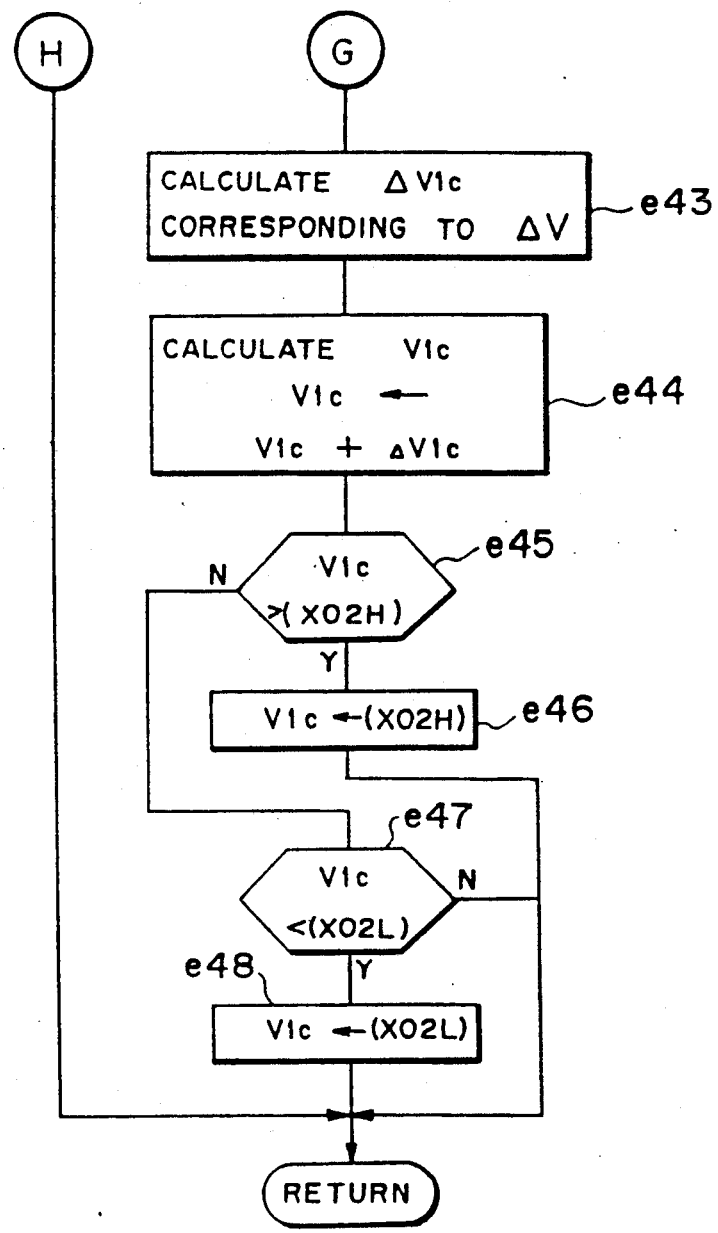

A description will next be made of the correction of the rich/lean-judging first reference value V1c. First of all, as illustrated in FIG. 11, ΔV1c corresponding to ΔV obtained in step e11 of FIG. 7 is calculated in step e43.

Figure 19A:
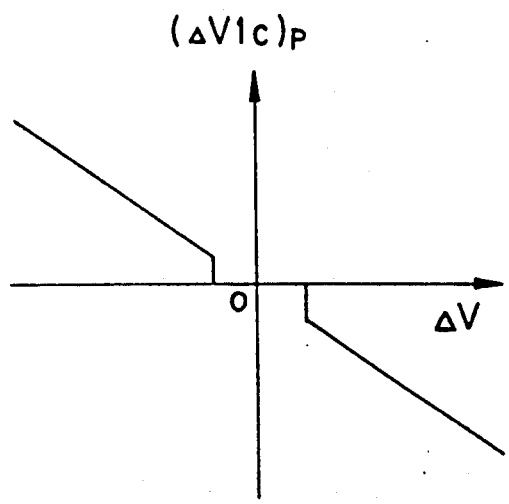
FIGS. 19(a) and 19(b) are respectively graphs for describing a correction value for a first reference value for rich/lean judgment to be compared with an output from an forward $O_2$ sensor.
Figure 19B:
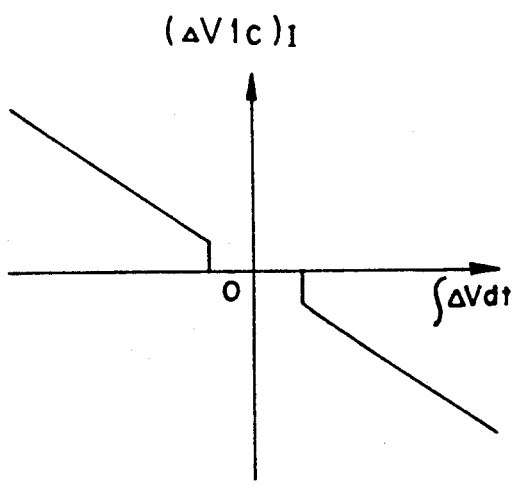

Correction characteristics for the ΔV1c may be illustrated as shown in FIGS. 19(a) and 19(b).

Namely, ΔV1c is given as the sum of {ΔV1c}$_P$ based on an integrated value of ΔV. It may hence be expressed as follows:

$$\Delta V1c = (\Delta V1c)_I + (\Delta V1c)_P$$

Functional relations (inclinations and dead zones shown in these FIGS. 19(a) and 19(b) are also set in the ROM data.

After determination of the ΔV1c in the above manner, the ΔV1c is added to the reference value (V1c)$_o$ of V1c in step e44, thereby determining new V1c.

In the next step e45, it is judged whether V1c is greater than XO2H (upper limit: this value is set in the ROM data; V1c > XO2H). If the answer is "NO", it is judged in step e47 whether V1c is smaller than XO2L (lower limit: this value is set in the ROM data; V1c < XO2L).

If the answer is "YES" in step e45, XO2H is set as V1c in step e46. If the answer is "YES" in step e47, XO2L is set as V1c in step e48.

If the answer is "NO" in step e47 or after the processings of steps e46,e48, the routine returns.

Figures 26A, 26B, 26C, 27A, 27B, 27C:
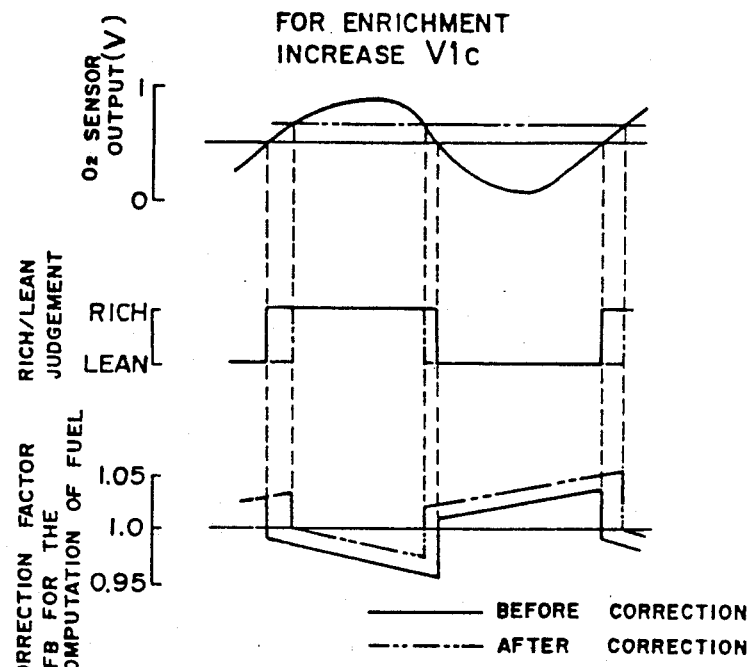

When V1c is corrected on the basis of the output V2 of the rearward $O_2$ sensor and the air/fuel ratio is rendered richer, V1c is rendered greater as illustrated in FIGS. 26(a) through 26(c). For rendering the air/fuel ratio leaner, V1c is rendered smaller as shown in FIGS. 27(a) through 27(c).

As has been described above, the output V2 of the rearward $O_2$ sensor 18 is measured during the air/fuel ratio feedback control at constant time intervals (or whenever the output V1 of the forward $O_2$ sensor 17 crosses the first reference value V1c) and the correction of the rich/lean-judging reference value V1c is effected to make its moving average equal to V2c whereby the air/fuel ratio is corrected.

Accordingly, the accuracy of the control does not vary even by variations in characteristics from one $O_2$ sensor to another and variations of the characteristics of the $O_2$ sensor along the passage of time and moreover, the cleaning efficiency of exhaust gas by the catalytic converter 9 is maintained high. High control reliability can thus be assured.

Even when EGR is not performed or even when EGR is performed but at a low rate, a good exhaust gas quality level is achieved. The EGR system can therefore be simplified and in addition, the power performance and drivability are not sacrificed by exhaust gas.

Further, the output V2 of the rearward $O_2$ sensor 18 is measured during the air/fuel ratio feedback control at constant time intervals (or wherever the output V1 of the forward $O_2$ sensor 17 crosses the first reference value V1c) and the corrections of the response delay time, integral gain, proportional gain and rich/lean-judging reference value are effected to make its moving average equal to V2c, whereby the air/fuel ratio is corrected. The air/fuel ratio control can therefore be performed with still higher reliability and accuracy.

Incidentally, in the first embodiment described above, only one or some of the response delay times, integral gains, proportional gains and rich/lean-judging reference value may be corrected in such a way that the moving average of the output V2 of the rearward $O_2$ sensor 18 becomes equal to V2c.

Figure 28A:
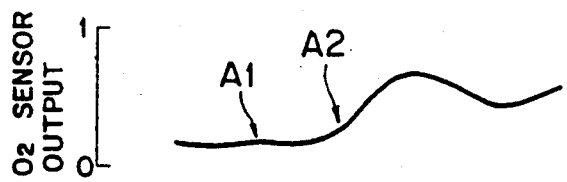
FIGS. 28(a) through 28(c) diagrammatically illustrate effects of the control upon acceleration.
Figure 28B:
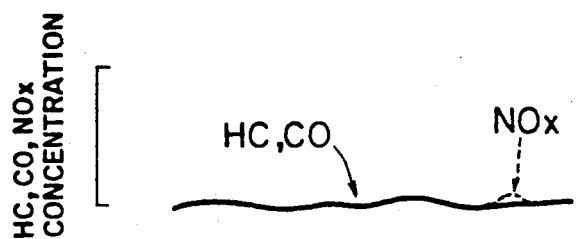
Figure 28C:
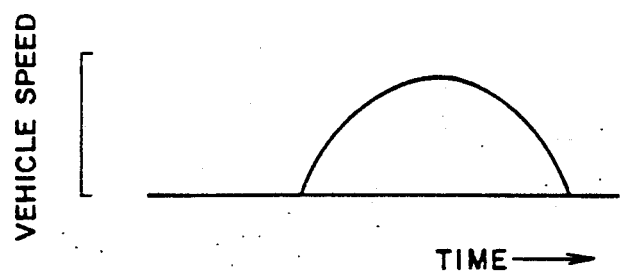

Even when the engine is in an $O_2$ feedback operation state, the reference value V1c to be compared with the detection value from the forward $O_2$ sensor is changed to the second reference value V1c' (for example, 0.3 volt) shifted to the lean air/fuel ratio side in a low-load operation state of small intake-air-quantity operation state of the engine such as an idling state. Accordingly, the output of the rearward $O_2$ sensor 18, in other words, the exhaust gas flowing into the catalytic converter 9 is always in a lean state [see A1 of FIG. 28(a)]. Incidentally, in this state, the NOx component emitted is so little that it can be ignored, because the flow rate of exhaust gas is low or the combustion temperature is relatively low. Let's think of the situation that acceleration is effected from such a lean state as illustrated in FIG. 28(c). Since the catalytic converter 9 is in an oxygen-excessive state before the acceleration, this excessive oxygen and HC and CO emitted from the engine react so that the emission of HC and CO is reduced immediately after the acceleration (see the characteristic curve shown by a solid line in FIG. 28(b)]. Owing also to the O₂ sensor control using the reference voltage changed to the first reference value V1c the catalytic converter 9 is in a rich state after the acceleration. The efficiency of purification for NOx is therefore improved and, as a result, the amount of NOx to be emitted form the vehicle can be reduced [see the characteristic curve shown by broken lines in FIG. 28(b)].

Figure 29:
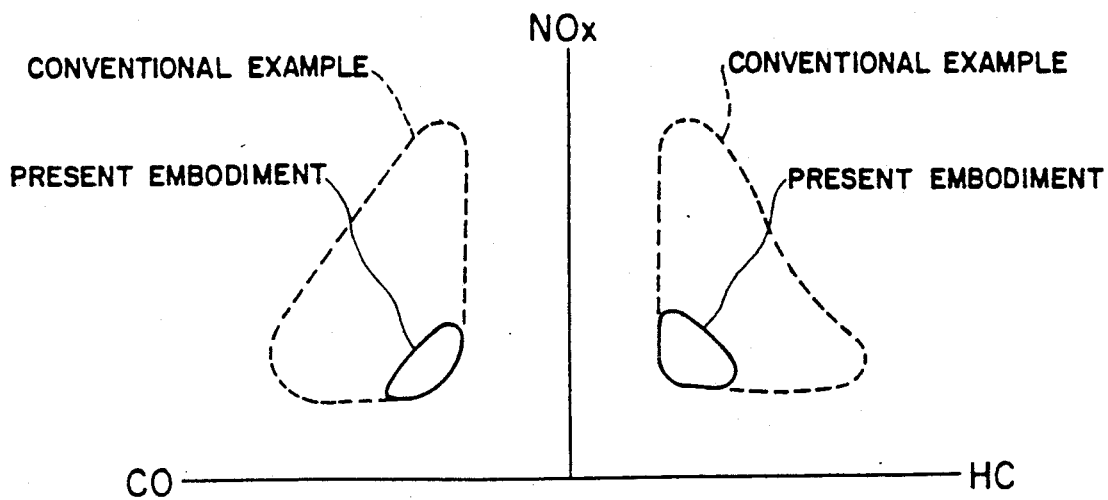

Effects in an actual exhaust gas mode are illustrated in FIG. 29. As is also seen from FIG. 29, the present embodiment can reduce all of HC, CO and NOx (see the area indicated by the solid line in FIG. 29), while in the conventional example described above, a reduction of any one of HC, CO and NOx results in an increase of at least one of the remaining ones and it is impossible to reduce all of HC, CO and NOx (see the area indicated by the dashed line in FIG. 29).

In addition, the high reliability of the control is not impaired because corrections of the response delay times DLYRL,DLYLR, proportional gains $P_{RL}, P_{LR}$, integral gains $I_{RL}, I_{LR}$ and rich/lean-judging reference value V1c on the basis of the deviation $\Delta V$ of the output V2 from the rearward O₂ sensor from the reference value V2c for the rearward O₂ sensor is prohibited in a small intake-air-quantity operation state.

Further, since the rearward O₂ sensor 18 is provided on the rearward side of or inside the catalytic converter 9, unburnt components in exhaust gas are reduced and the control λ point (the point at which the output of the O₂ sensor 18 presents a sudden change) approaches the theoretical air/fuel ratio, and further, fluctuations in the emission level are reduced. In addition, since the influence of a delay in response inherent to the engine system can be eliminated, a good exhaust gas purifying characteristic can also be expected from the point.

An air/fuel ratio control system according to a second embodiment will next be described with reference to FIGS. 30 and 31.

In the second embodiment, the output V2 of the rearward O₂ sensor 18 is measured during the air/fuel ratio feedback control and another feedback correction factor $K_{FB2}$ different from the above-described feedback correction factor $K_{FB}$ is obtained on the basis of the output V2. Namely, the correction factor $K_{FB2}$ is obtained from a map or by computation in accordance with $\Delta V$ determined in FIG. 7 (see step e49 of FIG. 31).

Figure 30:
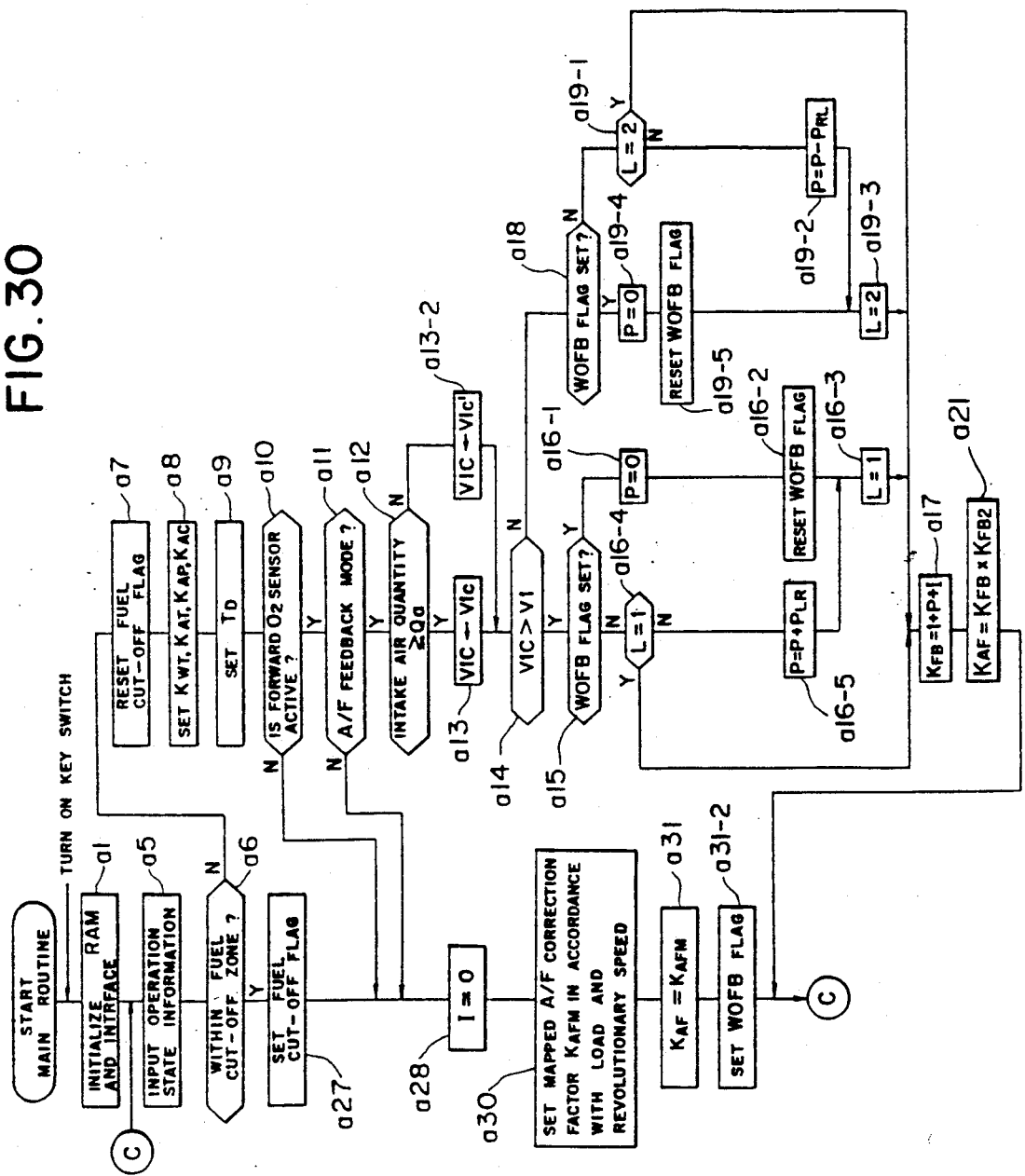
Figure 31:
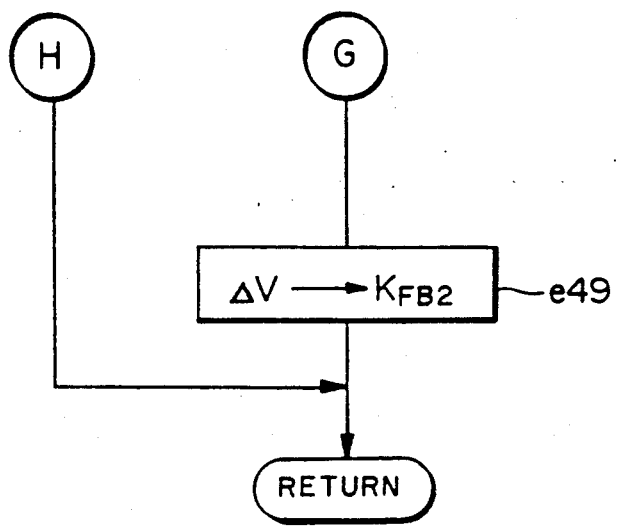

In this case, the correction factor $K_{FB}$ determined in step a17 of FIG. 30 is multiplied with the correction factor $K_{FB2}$, which has been obtained in FIG. 31, in step a21 of FIG. 30 so as to use the resulting product as $K_{FB}$.

The other parts of the main flow are identical to their corresponding parts illustrated in FIG. 4 except for the omission of steps a16-4' and a19-1'.

In this manner, it is also possible to obtain substantially the same effects and advantages as those obtained by the first embodiment.

An air/fuel ratio control system according to a third embodiment of the present invention will hereinafter be described with reference to FIGS. 32 through 46.

Figure 32:
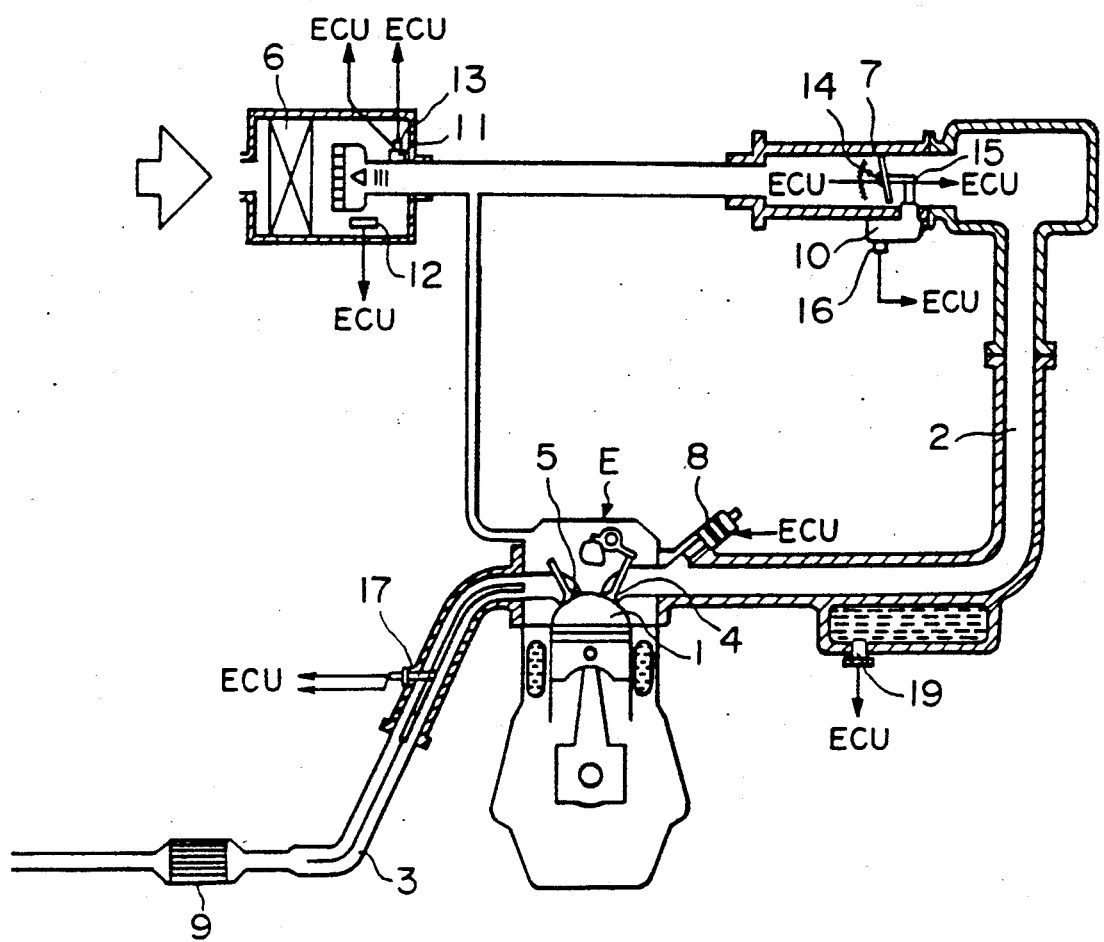

In this third embodiment, as shown in FIG. 32, the O₂ sensor 18 on the rearward side of the catalytic converter 9 is omitted and, instead, an O₂ sensor 17 having two O₂ sensor elements (first sensing element 17A and second sensing element 17B) is provided on the forward side of the catalytic converter 9. One of these two O₂ sensor elements in the O₂ sensor 17, i.e., the second sensing element 17B has been improved so that the second sensing element 17B has substantially the same function as the rearward O₂ sensor.

Accordingly, it is only necessary to substitute the first and second sensing element 17A,17B for the forward and rearward O₂ sensors 17,18 in the first and second embodiments described above. The air/fuel ratio is therefore controlled on the basis of the results of a comparison between a detection value V1 from the first sensing element 17A and a predetermined reference value V1c. As the reference value, V1c of about 0.5 volt by way of example is chosen in operation states other than the low-speed and low-load operation state. V1c' of about 0.3 volt by way of example is chosen in the low-speed and low-load operation state. Further, the response delay times, integral gains, proportional gains and rich/lean-judging first reference value V1c are corrected based on the deviation $\Delta V$ of the detection value V2 by the second sensing element 17B from the reference value V2c. Similarly to the first and second embodiments described above, the corrections by the deviation $\Delta V$ of the detection value V2 of the second sensing element 17B from the reference value V2c are prohibited in the low-speed and low-load operation state.

To convert the above-described drawings of the first embodiment to those of the third embodiment, it is only necessary to change the reference symbol of the first air/fuel ratio detection means to the reference symbol, 17A, of the first sensing element and the reference symbol of the second air/fuel detection means to the reference symbol, 17B, of the second sensing element in FIG. 1(a); the forward O₂ sensor 17 to the first sensing element 17A and the rearward O₂ sensor 18 to the second sensing element 17B in FIGS. 1(b) and 2; step a10 to "IS FIRST SENSING ELEMENT 17A ACTIVE?" in FIG. 4; and "FORWARD AND REARWARD O₂ SENSORS" to "FIRST AND SECOND SENSING ELEMENTS" in steps e1, e6 and e7 of FIG. 7.

Further, to convert the drawings of the second embodiment to those of the third embodiment, it is only necessary to change step a10 to "IS FIRST SENSING ELEMENT ACTIVE?" in FIG. 30.

Figure 33:
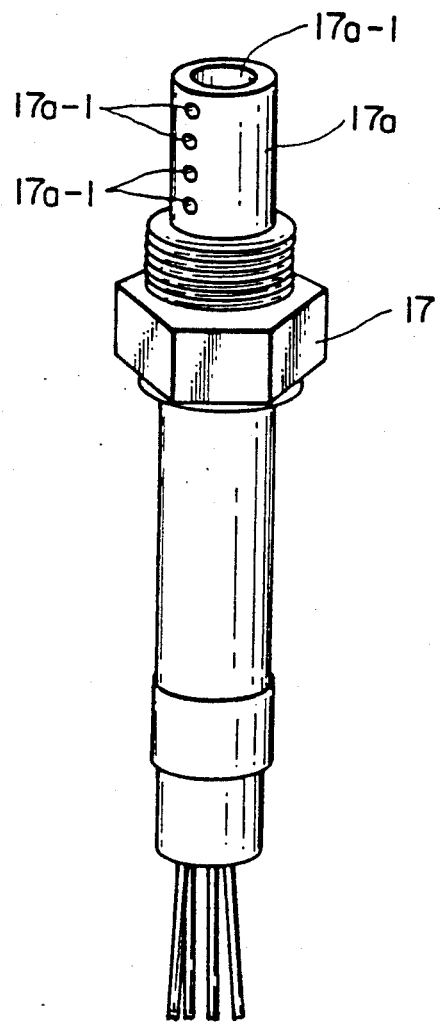
Figure 34:
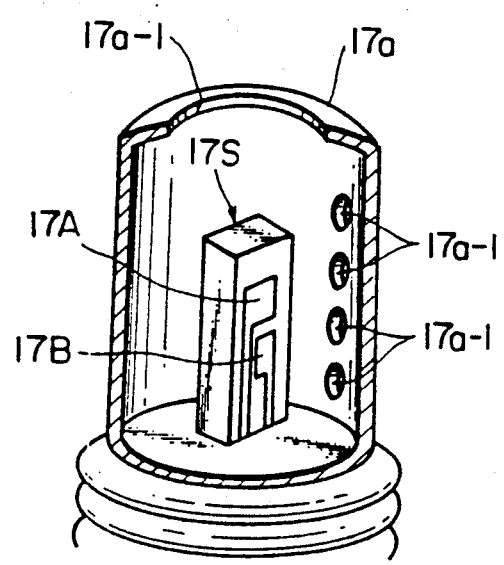
Figure 35:
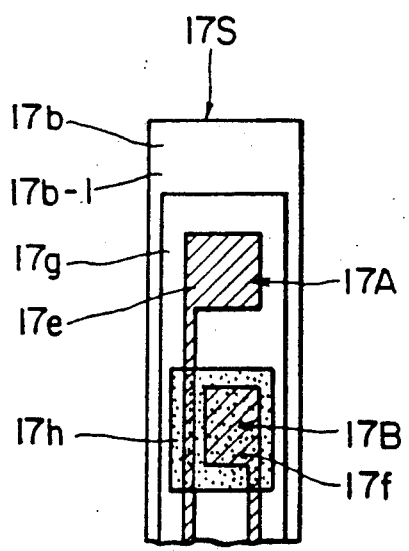

A description will next be made of the O₂ sensor 17 of the two-element built-in type employed in the third embodiment. The O₂ sensor 17 has an external appearance as shown in FIG. 33. As depicted in FIG. 34, the O₂ sensor 17 has the structure that a sensor element portion 17S, which is to be arranged within the exhaust passage 3, is located at a tip portion of the O₂ sensor and is covered by a protective cover 17a. Plural communication holes 17a-1 are formed through the protective cover 17a to communicate the exhaust passage 3 with a space in which the sensor element portion is arranged.

As shown in FIGS. 34 through 37, the O₂ sensor 17 is equipped with a first sensing element 17A as a first O₂ sensor element for detecting the density of oxygen in exhaust gas and a second sensing element 17B as a second O₂ sensor element having a slower oxygen density detection response speed compared to the first sensing element 17A. These first sensing element 17A and second sensing element 17B are provided on a common base member 17b.

Namely, the O₂ sensor 17 has the base member 17b made of a solid electrolyte such as $ZrO_2$. On an exhaust-gas-side wall 17b-1 of the base member 17b, there are provided a first measuring electrode 17e, and a second measuring electrode 17f covered with a catalyst layer 17h which contains Pt and/or Rh. Reference electrodes 17i,17j are provided on an atmosphere-side wall 17b-2 of the base member 17b in an opposed relation with these measuring electrodes 17e,17f, respectively. The surface of each of the measuring electrodes 17e,17f is covered with a coating layer 17g made of alumina or the like. The catalyst layer 17h covers the second measuring electrode 17f with the coating layer 17g interposed therebetween. Incidentally, the first and second measuring electrodes 17e,17f and the reference electrodes 17i,17j are all formed of Pt which is suitable for the formation of electrodes for an oxygen concentration cell.

The first sensing element 17A is constructed of the first measuring electrode 17e, the reference electrode 17i and the solid electrolyte (a portion of the base member 17b) located between these electrodes. The second sensing element 17B is constructed of the second measuring electrode 17f having the catalyst layer 17h, the reference electrode 17j and the solid electrolyte (another portion of the base member 17b) located between these electrodes.

Accordingly, the first sensing element 17A is constructed as a sensing element concentrating the importance on the responsibility, in other words, having small catalytic ability like the conventional art. On the other hand, the second sensing element 17B has catalytic ability improved over the first sensing element owing to the provision of the catalyst layer 17h while its responsibility is slower relative to the first sensing element. It is hence possible to exclude non-equilibrated components which are contained in exhaust gas and would otherwise reach the electrode, thereby making it possible to shift the static λ point toward the stoichiometric point, in other words, to reduce variations of the static λ point and dynamic λ point. Namely, the second sensing element 17B can show exactly the same function as the conventional rearward $O_2$ sensor although it is located on the upstream side of the catalytic converter 9.

Figure 36:
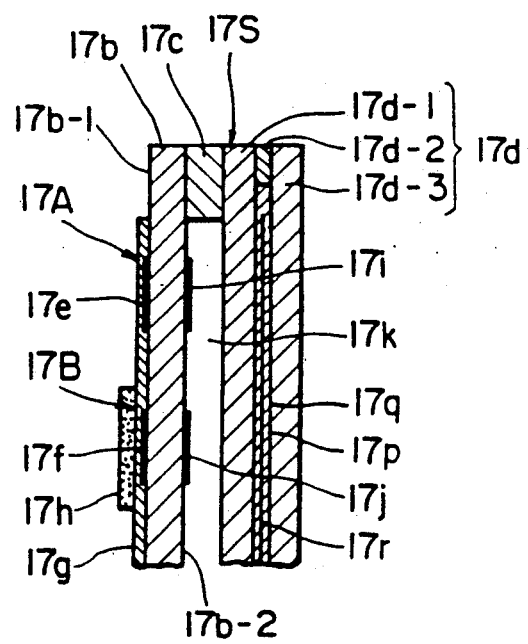
Figure 37:
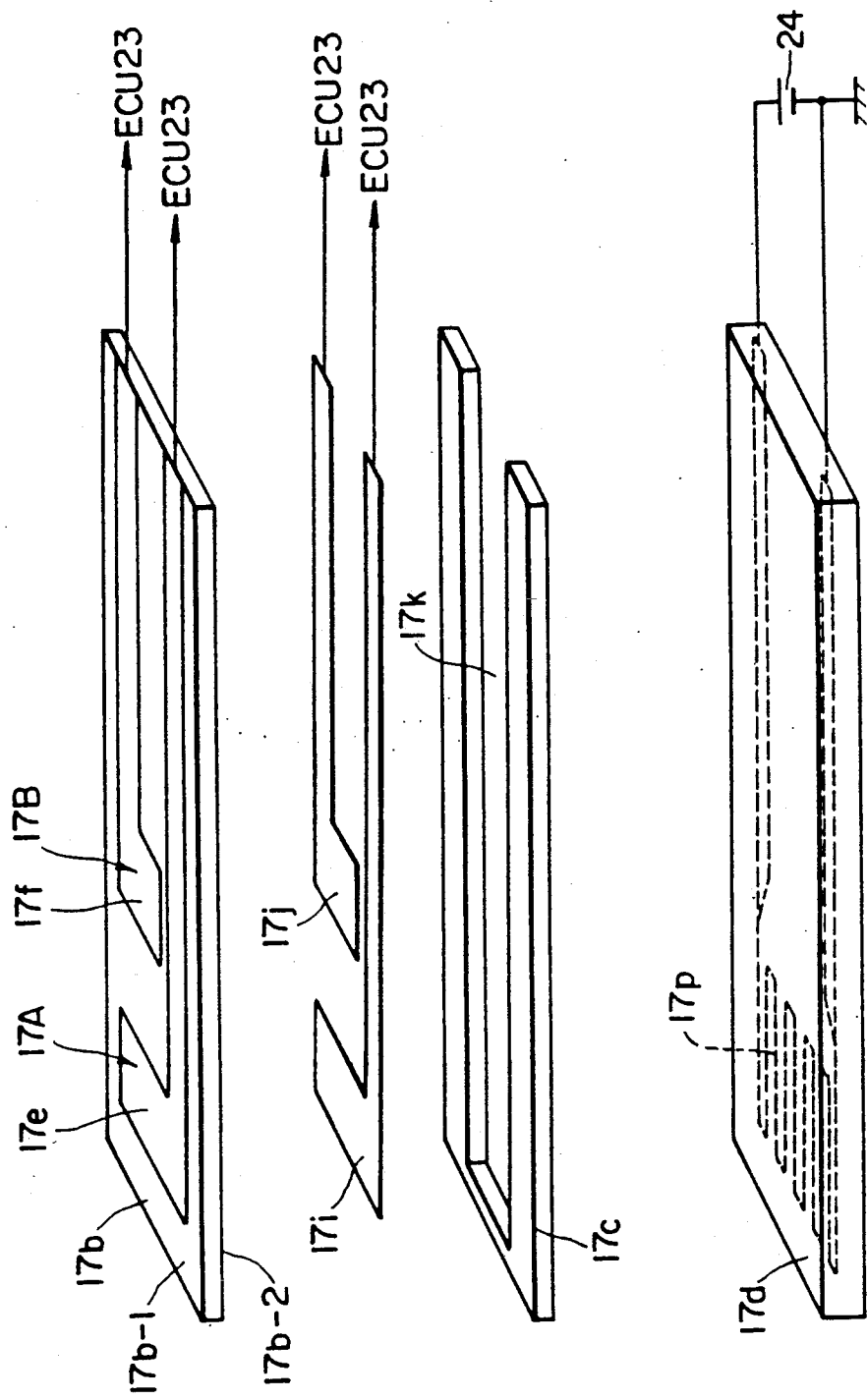

The $O_2$ sensor 17 is constructed as an $O_2$ sensor of the stacked type. Namely, the $O_2$ sensor 17 has been formed by stacking five plate-like members 17b,17c,17d-1,17d-2,17d-3 which are each made of a solid electrolyte such as $ZrO_2$. Of these plate-like members, the one arranged on the most left-hand side as viewed in FIG. 36 is formed as the base member 17b. As has been described above, the measuring electrodes 17e,17f and reference electrodes 17i,17j are provided on the base member 17b.

Among these plate-like members, the three plate-like members 17d-1,17d-2,17d-3 arranged on the opposite side are formed as a heater base member assembly 17d. This heater base member assembly 17d is provided with a heater 17p. Describing this heater base member assembly 17d further, it has been assembled by printing the heater 17p on one of the plate-like members, for example, the plate-like member 17d-1, fitting the heater 17p in a punched-out portion of the central plate-like member 17d-2 and then superposing the remaining plate-like member 17d-3 thereon.

The heater 17p has a heater element 17r coated with an insulating layer 17q formed of $Al_2O_3$. The insulating layer 17q and heater element 17r are both formed by a printing technique. For the fabrication of the heater, a part of the insulating layer 17q is printed first, the heater element 17r is printed over the part of the insulating layer, and the remaining part of the insulating layer 17q is thereafter printed over the heater element.

On the other hand, the intermediately-arranged plate-like member out of the plate-like members, namely, the intermediate member 17c has the punched-out portion. By superposing these five plate-like members 17b,17c,17d-1,17d-2,17d-3, the punched-out portion forms a reference air introducing chamber 17k which is in communication with the atmosphere. In this superposed state, the reference electrodes 17i,17j are located facing the reference air introducing chamber 17k.

The first sensing element 17A and second sensing element 17B independently form voltage detection circuits.

The heater 17p is connected to a battery 24 via an unillustrated switch.

In the manner described above, it is possible to arrange and house in a compact manner the first sensing element 17A and second sensing element 17B within the single sensor element portion 17S. The above fabrication method has made it possible to provide sophisticated sensors with ease.

Since the sensing elements are both arranged under substantially the same temperature conditions, the sensor does not develop such inconvenience as experienced with the conventional dual $O_2$ sensor systems described above. Since the temperature of the second sensing element 17B equivalent to the downstream $O_2$ sensor 18 can be raised to a level substantially equal to the temperature of the first sensing element 17A, it is possible to avoid the inconvenience that the output of the second sensing element 17B is not stable although the output of the first sensing element 17A is stable.

The fabrication process of the $O_2$ sensor 17 of the stacked type, namely, the fabrication process of the thin film will next be described with reference to FIGS. 38(a)-38(e) and FIGS. 39(a)-39(e).

Figure 38A:
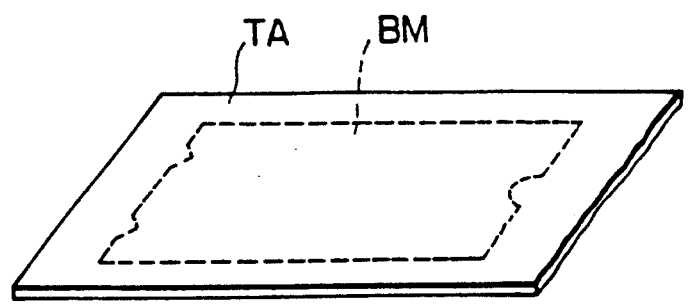
FIGS. 38(a) through 38(e) illustrate $O_2$ sensor in various steps of its fabrication process.
Figure 39A:
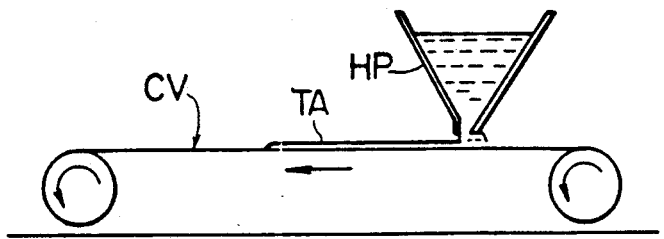
FIG. 39(a) through 39(e) correspond to FIGS. 38(a) through 38(e) and depict the various steps of the fabrication process of the sensor.

First of all, a board BM as a stock material for the plate-like members 17b,17c,17d-1,17d-2,17d-3 is formed from a tape TA [see FIG. 38(a)]. FIG. 39(a) is a schematic illustration showing the manner for forming the tape TA. A mixture of powder of a solid electrolyte (ceramic powder), an organic binder and a solvent is charged in a hopper HP and is then fed onto a conveyor CV through a slit formed at a lower extremity of the hopper HP, whereby the tape TA is formed.

Figure 38B:
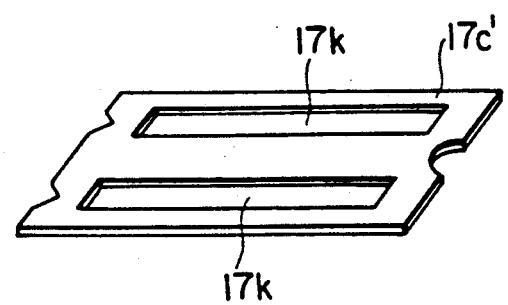
Figure 39B:
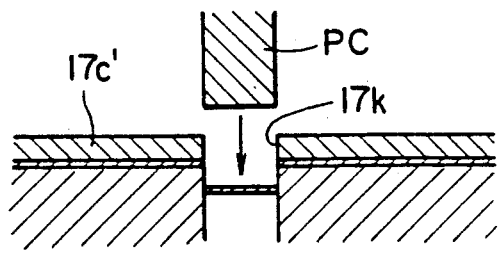

A portion of the board, which becomes the reference air introducing chamber 17k, is punched out by a punch PC, thereby forming a board 17c' for the intermediate member [see FIG. 38(b) and FIG. 39(b)].

Figure 38C:
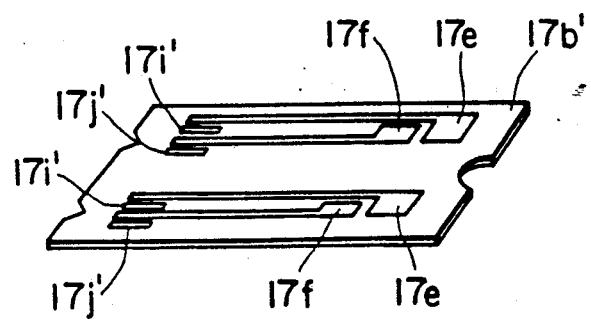
Figure 39C:
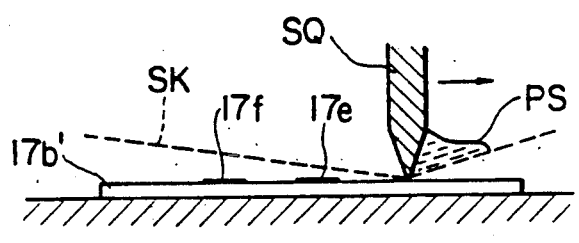

Along with this step, as shown in FIG. 38(c) and FIG. 39(c), a screen SK defining a desired printing pattern cut out therethrough is applied to one side of another board and a squeegee SQ is moved to coat the surface of the board with a paste PS. The first and second measuring electrodes 17e,17f are printed on the surface of the board, and the reference electrodes 17i,17j are also printed on the opposite side of the board in the same manner. Regarding this board, the coating layer 17g is then printed over the measuring electrodes in the same manner. Likewise, the catalyst layer 17h is also printed to cover the second measuring electrode 17f. A board 17b' for the base member has now been formed. Incidentally, conductor portions 17i',17j' which should be electrically connected to the reference electrodes 17i,17j respectively are printed similarly on the surface of the board 17b', said surface being on the side of the measuring electrodes. Holes are then formed through the board 17b' to electrically connect the conductor portions 17i',17j' to lead portions of the corresponding reference electrodes 17i,17j, respectively.

Along with the step in which a board 17c' for the intermediate member and another board 17b' for the base member, three boards for the heater base or a board assembly 17d' for the heater base member constructed of three boards for the heater base member is also formed. Although not illustrated in the drawings, the insulating layer 17q and heater element 17r are printed in a similar manner as in the formation of the electrodes by using the screen SK and squeegee SQ. Namely, a part of the insulating layer 17g is printed on the board, the heater element 17r is printed over the part of the insulating layer, and the remaining part of the insulating layer 17q is thereafter printed over the heater element. By the printing of the insulating layer 17g and heater element 17r, the heater 17p is fabricated by the printing technique. Thereafter, the heater 17p is fitted in the punched-out portion of the board for the intermediate heater base member and the other board for the heater base member is superposed to form the board assembly for the heater base member. As will be described subsequently, the board assembly 17d' for the heater base member is produced at the same time as it is stacked with the board 17c' for the intermediate member and the board 17b' for the base member. In addition, an overcoat layer is also printed.

Figure 38D:
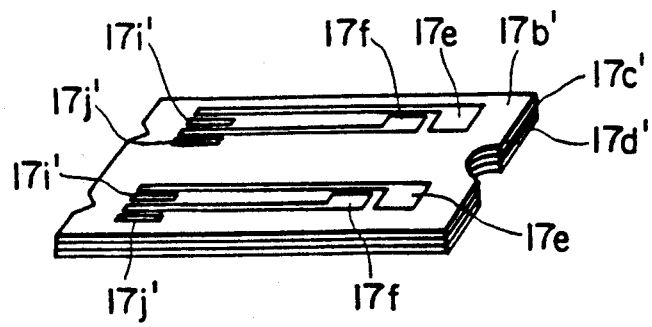
Figure 39D:
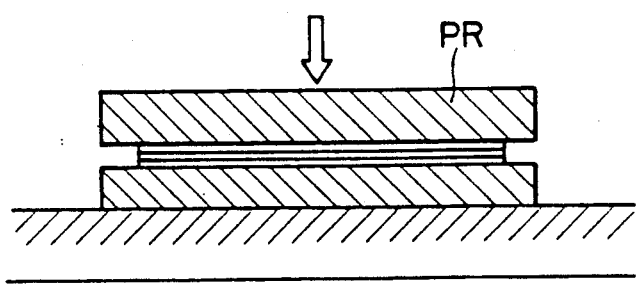

Thereafter, these boards are superposed and pressed by a press PR as shown in FIG. 39(d). By this step, the boards 17b',17c',17d' are bonded and stacked together under pressure as illustrated in FIG. 38(d).

Figure 38E:
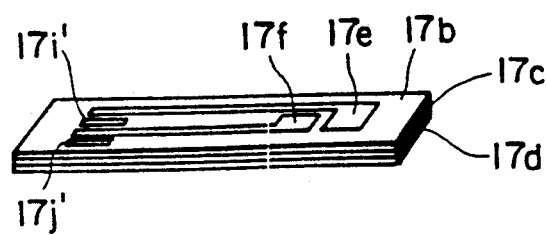
Figure 39E:
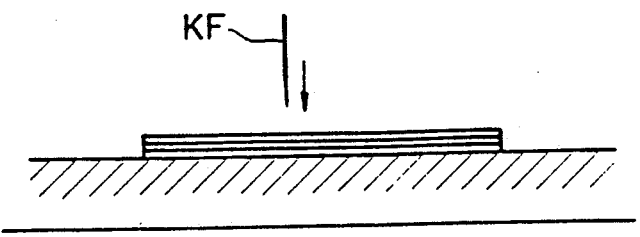

After then, as depicted in FIG. 39(e), the stacked boards shown in FIG. 38(d) are cut suitably by a knife KF. The product thus formed [see FIG. 38(e)] is then co-fired, thereby forming the sensor element portion 17S which constitutes the heart of the $O_2$ sensor.

Incidentally, the board assembly 17d' for the heater base member is illustrated as if it in the form of a single sheet in FIGS. 38(d) and 38(e). In fact, it has a three-layer structure as mentioned above.

Suitable wirings are thereafter applied to the sensor element portion 17S, followed by its packaging in a case or housing to complete the $O_2$ sensor 17.

Paying attention to the fabrication process of the $O_2$ sensor, the $O_2$ sensor 17 can be fabricated by only adding the printing step of the catalyst layer 17h. The $O_2$ sensor is therefore advantageous in fabrication cost compared to conventional dual $O_2$ sensor systems.

Figure 42:
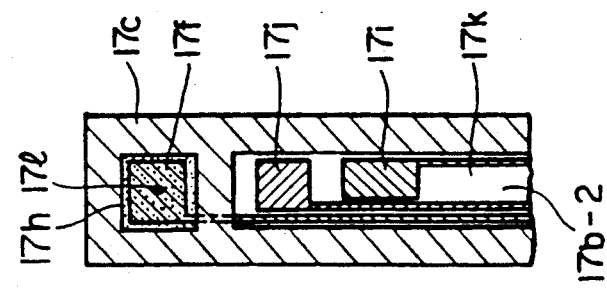
Figure 41:
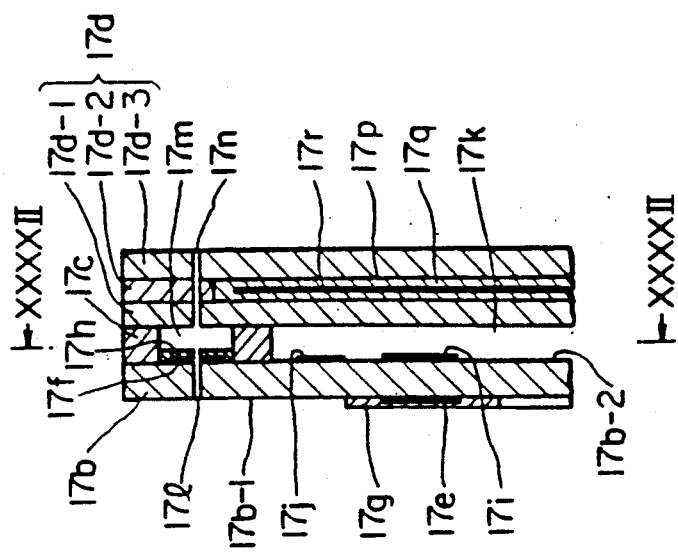
Figure 40:
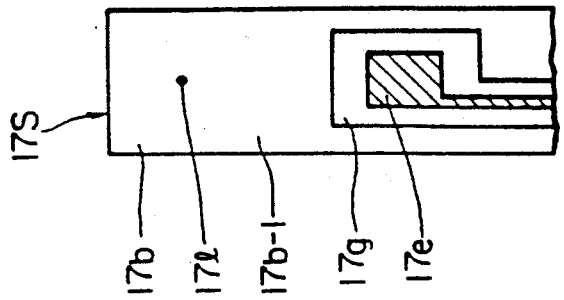

As the $O_2$ sensor 17, it is possible to use an $O_2$ sensor of a structure as shown in FIGS. 40–42 instead of using an $O_2$ sensor having such a sensor element portion as described above.

As illustrated in FIGS. 40–42, the $O_2$ sensor 17 is constructed of the base member 17b made of a solid electrolyte, the first measuring electrode 17e provided on the side wall 17b-1 of the base member 17b, said side wall 17b-1 being to be positioned on the side of exhaust gas, a diffusion chamber 17m formed in the base member 17b and adapted to receive exhaust gas through small-diameter passages 17l,17n, the second measuring electrode 17f disposed in the diffusion chamber 17m, the catalyst 17h arranged in the diffusion chamber 17m and covering the second measuring electrode 17f, and the reference electrodes 17i,17j provided corresponding to the respective measuring electrodes 17e,17f on the wall portion 17b-2 of the base member, said wall portion 17b-2 being to be positioned on the side of the atmosphere.

The first sensing element 17A is constructed of the first measuring electrode 17e, the reference electrode 17i and the solid electrolyte (a portion of the base member 17b) located between these electrodes. The second sensing element 17B is constructed of the second measuring electrode 17f having the catalyst layer 17h, the reference electrode 17j and the solid electrolyte (another portion of the base member 17b) located substantially between these electrodes.

Accordingly, the first sensing element 17A is constructed as a sensing element concentrating the importance on the responsibility, in other words, having small catalytic ability like the conventional art. On the other hand, the second sensing element 17B has catalytic ability improved over the first sensing element owing to the provision of the catalyst layer 17h although its responsibility is slower relative to the first sensing element. Therefore, it is also possible to exclude non-equilibrated components which are contained in exhaust gas and would otherwise reach the electrode, thereby making it possible to shift the static λ point toward the stoichiometric point, in other words, to reduce variations of the static λ point and dynamic λ point. Namely, the second sensing element 17B can also show exactly the same function as conventional rearward $O_2$ sensors although it is located on the upstream side of the catalytic converter 9.

The $O_2$ sensor 17 is also constructed as an $O_2$ sensor of the stacked type. Namely, the $O_2$ sensor 17 has been formed by stacking five plate-like members 17b,17c,17d-1,17d-2,17d-3 which are each made of a solid electrolyte such as $ZrO_2$. Of these plate-like members, the one arranged on the most left-hand side as viewed in FIG. 41 is formed as the base member 17b. As has been described above, the measuring electrodes 17e,17f and reference electrodes 17i,17j are provided on the base member 17b.

Among these plate-like members, the three plate-like members 17d-1,17d-2,17d-3 arranged on the opposite side are formed as the heater base member assembly 17d. This heater base member assembly 17d is provided with the heater 17p. Describing this heater base member assembly 17d further, it has been assembled by printing the heater 17p on one of the plate-like members, for example, the plate-like member 17d-1, fitting the heater 17p in the punched-out portion of the central plate-like member 17d-2 and then superposing the remaining plate-like member 17d-3 thereon.

The heater 17p has the heater element 17r coated with the insulating layer 17q formed of $Al_2O_3$. The insulating layer 17q and heater element 17r are both formed by a printing technique. For the fabrication of the heater, a part of the insulating layer 17q is printed first, the heater element 17r is printed over the part of the insulating layer, and the remaining part of the insulating layer 17q is thereafter printed over the heater element.

On the other hand, the intermediately-arranged plate-like member out of the plate-like members, namely, the intermediate member 17c has two punched-out portions. By superposing these five plate-like members 17b,17c,17d-1,17d-2,17d-3, one of the punched-out portions forms the reference air introducing chamber 17k communicated to the atmosphere and the other punched-out portion forms the diffusion chamber 17m. In this superposed state, the reference electrodes 17i,17j are located facing the reference air introducing chamber 17k and the second measuring electrode 17f is positioned facing the diffusion chamber 17m.

Here again, the first sensing element 17A and second sensing element 17B independently form voltage detection circuits. The heater 18 is connected to the battery 24 via the unillustrated switch.

In the manner described above, it is also possible, in the case of the O$_2$ sensor 17 depicted in FIGS. 40–42, to arrange and house in a compact manner the first sensing element 17A and second sensing element 17B within the single sensor element portion 17S. The above fabrication method has also made it possible to provide a sophisticated sensor with ease.

Since the sensing elements are both arranged under substantially the same temperature conditions, the sensor does not develop such inconvenience as experienced with the conventional dual O$_2$ sensor systems described above.

The fabrication process of the O$_2$ sensor 17, namely, the fabrication process of the thin film will next be described with reference to FIGS. 43(a)–43(f).

Figure 43A:
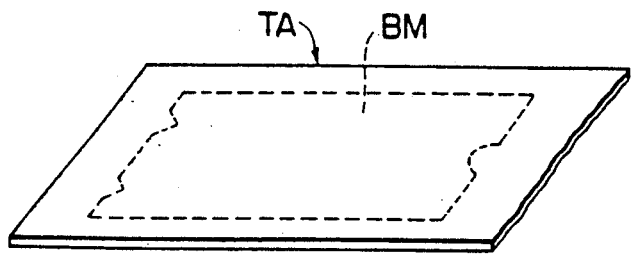
FIGS. 43(a) through 43(f) illustrate the $O_2$ sensor in various steps of its fabrication process.

First of all, the board BM as the stock material for the plate-like members 17c,17d-1,17d-2,17d-3 is formed from the tape TA [see FIG. 43(a)].

Figure 43B:
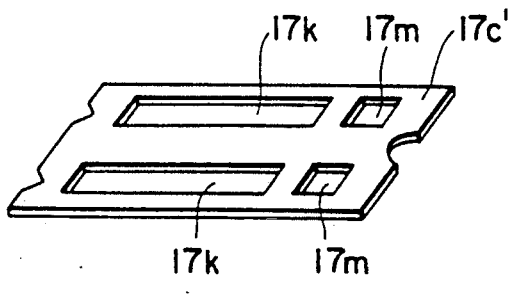

The portions of the board, which become the reference air introducing chamber 17k and diffusion chamber 17m respectively, are punched out by the punch PC, thereby forming a board 17c' for the intermediate member [see FIG. 43(b)].

Figure 43C:
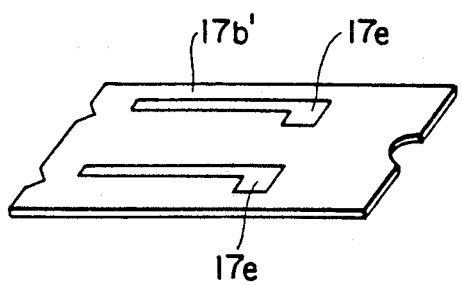

Along with this step, as shown in FIG. 43(c), a screen SK defining a desired printing pattern cut out therethrough is applied to one side of another board and the squeegee SQ is moved to coat the surface of the board with the paste PS [this procedure is the same as that shown in FIG. 39(a)]. As illustrated in FIG. 43(d), the first measuring electrode 17e is printed on the surface of the board, and the second measuring electrode 17f and reference electrodes 17i,17j are also printed on the opposite side of the board in the same manner. Regarding this board, the coating layer 17g is then printed over the first measuring electrode 17e in the same manner. Likewise, the catalyst layer 17h is also printed to cover the second measuring electrode 17f. The board 17b' for the base member has now been formed.

Along with the step in which the board 17c' for the intermediate member and the board 17b' for the base member, three boards for the heater base or the board assembly 17d' for the heater base member constructed of three boards for the heater base member is also formed. Although not illustrated in the drawing, these steps are similar to the above-described embodiment and their description is omitted herein.

Thereafter, these boards are superposed and pressed. By this step, the boards 17b',17c',17d' are bonded and stacked together under pressure as illustrated in FIG. 43(e).

Figure 43E:
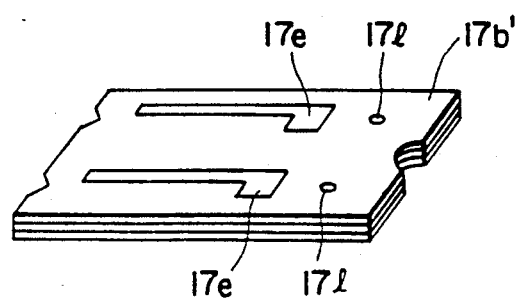

After then, the stacked boards shown in FIG. 43(e) are cut suitably by a knife. The product thus formed [see FIG. 43(f)] is then co-fired, thereby forming the sensor element portion 17S which constitutes the heart of the O$_2$ sensor 17.

Figure 43F:
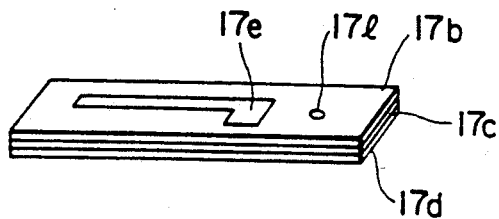
Figure 43D:
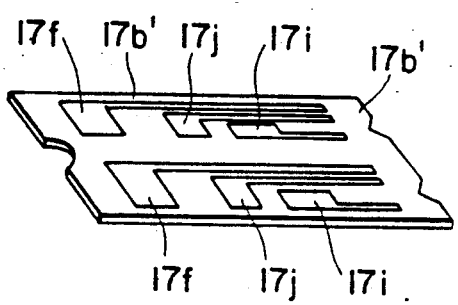

By the way, FIGS. 43(e) and 43(f) illustrate the board assembly 17d' for the heater base member as if it a single sheet. However, the board assembly 17d' actually has the three-layer structure as described above.

Suitable wirings are then applied to the sensor element portion 17S, followed by package of the sensor element portion 17S in a casing or housing to complete the O$_2$ sensor 17.

Paying attention to the fabrication process of the O$_2$ sensor, the punching of the diffusion chamber 17m is conducted at the same time as the punching of the reference air introducing chamber 17k. No additional step is therefore needed practically. Correctly speaking, the O$_2$ sensor 17 can be fabricated by only adding the printing step of the catalyst layer 17h. The O$_2$ sensor is therefore advantageous in fabrication cost compared to conventional dual O$_2$ sensor systems.

Figure 46:
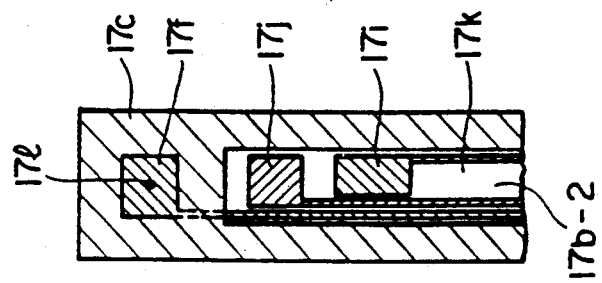
Figure 45:
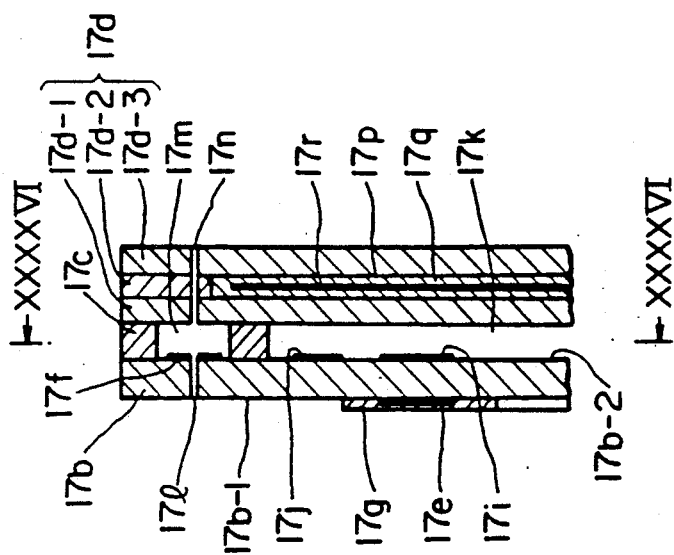
Figure 44:
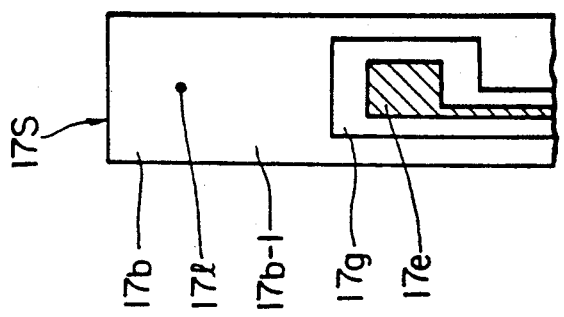

As the O$_2$ sensor 17, it is possible to use an O$_2$ sensor of a still different structure as shown in FIGS. 44–46 instead of using an O$_2$ sensor having such a sensor element portion as described above.

As illustrated in FIGS. 44–46, the O$_2$ sensor 17 of the still different structure is constructed of the base member 17b made of the solid electrolyte, the first measuring electrode 17e provided on the side wall 17b-1 of the base member 17b, said side wall 17b-1 being to be positioned on the side of exhaust gas, the diffusion chamber 17m formed in the base member 17b and adapted to receive exhaust gas through small-diameter passages 17l,17n, the second measuring electrode 17f disposed in the diffusion chamber 17m and having catalytic ability, and the reference electrodes 17i,17j provided corresponding to the respective measuring electrodes 17e,17f on the wall portion 17b-2 of the base member 17b, said wall portion 17b-2 being to be positioned on the side of the atmosphere.

The first sensing element 17A is constructed of first measuring electrode 17e, the reference electrode 17i and the solid electrolyte (a portion of the base member 17b) located between these electrodes. The second sensing element 17B is constructed of the second measuring electrode 17f having the catalytic ability, the reference electrode 17j and the solid electrolyte portion (another portion of the base member 17b) located substantially between these electrodes.

As is also envisaged from FIG. 44 through FIG. 46, the O$_2$ sensor 17 is different only at the portion of the second measuring electrode 17f compared to the O$_2$ sensor 17 shown in FIGS. 40–42. Namely, in the O$_2$ sensor 17 depicted in FIGS. 40–42, the second measuring electrode 17f is covered by the catalyst 17h. In the O$_2$ sensor 17 shown in FIGS. 44–46, the second measuring electrode 17f is not covered by any catalyst but the electrode itself has catalytic ability.

Accordingly, the first sensing element 17A is constructed as a sensing element concentrating the importance on the responsibility, in other words, having small catalytic ability like the conventional art. On the other hand, the second sensing element 17B has catalytic ability improved over the first sensing element owing to the provision of the measuring electrode 17f having large catalytic ability while its responsibility is slower compared to the first sensing element.

Therefore, it is also possible to exclude by the second sensing element 17B non-equilibrated components which are contained in exhaust gas and would otherwise reach the electrode, thereby making it possible to shift the static λ point toward the stoichiometric point, in other words, to reduce variations of the static λ point and dynamic λ point. Namely, the second sensing element 17B can also show exactly the same though it is located on the upstream side of the catalytic converter 9.

The manner of fabrication of the O$_2$ sensor 17 shown in FIGS. 44–46 is similar to that illustrated in FIGS. 43(a)-43(f). The merits of the fabrication process shown in FIGS. 43(a)-43(f) can also be obtained similarly.

Incidentally, hatching is applied to each electrode in FIGS. 35, 40, 42, 44 and 46. This hatching however does not indicate a cross-section but has been applied to show the existence of the electrode.

Instead of providing the reference electrodes 17*i*,17*j* separately corresponding to the first and second measuring electrodes 17*e*,17*f*, a single reference electrode may be provided commonly to the measuring electrodes.

As has been described above, it is also possible to obtain substantially the same effects and advantages as those of the first and second embodiments described above by eliminating the $O_2$ sensor 18 on the downstream side of the catalytic converter 9 and, instead, providing the $O_2$ sensor 17 having the two $O_2$ sensor elements (the first sensing element 17A and the second sensing element 17B) on the upstream side of the catalytic converter 9, and improving one (the second sensing element 17B) of the two $O_2$ sensor elements of the $O_2$ sensor 17 to allow the $O_2$ sensor 17 to have substantially the same function as the downstream $O_2$ sensor. Accordingly, the accuracy of the control does not vary even by variations in characteristics from one $O_2$ sensor to another and variations of the characteristics of the $O_2$ sensor along the passage of time and moreover, the cleaning efficiency of exhaust gas by the catalytic converter 9 is maintained high. High control reliability can thus be assured.

In addition, like the first and second embodiments described above, the reference value to be compared with a detection value from the first sensing element 17A is shifted to the air/fuel ratio side in the small intake-air-quantity operation state. It is therefore possible to avoid deterioration of the efficiency of purification for HC, CO and NOx by the catalytic converter even when acceleration is performed from the small intake-air-quantity operation state.

Further, the high reliability of the control is not impaired because the corrections of the response delay times $DLY_{RL}, DLY_{LR}$, proportional gains $P_{RL}, P_{LR}$, integral gains $I_{RL}, I_{LR}$ and rich/lean-judging reference value V1c on the basis of the deviation $\Delta V$ of the output V2 of the second sensing element 17B from the reference value V2c for the second sensing element are prohibited.

It is possible to use, as $O_2$ sensors, those of type other than the stacked type. Instead of the first and second $O_2$ sensors integrated together, first and second $O_2$ sensors enclosed in separate casings may also be used.

An air/fuel ratio according to a fourth embodiment of the present invention will now be described with reference to FIGS. 47 through 51.

Figure 47:
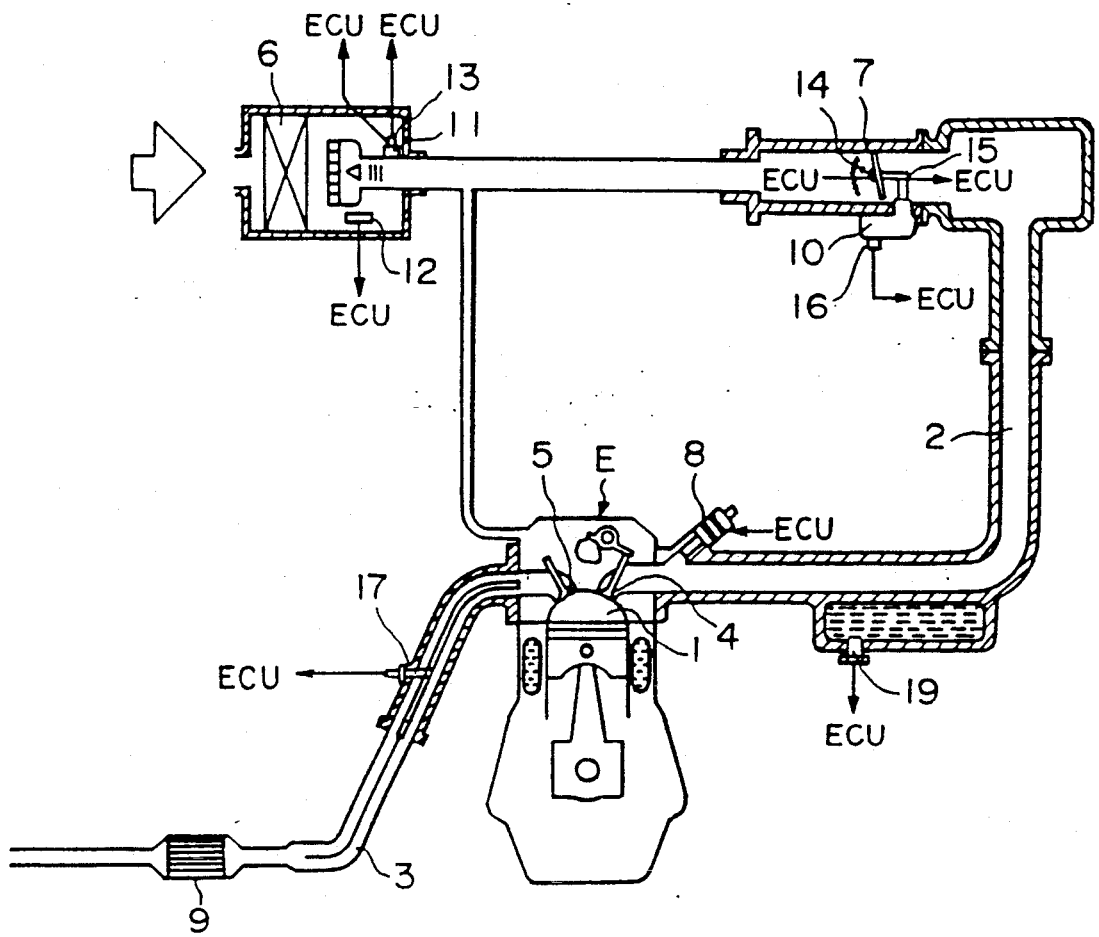
Figure 48:
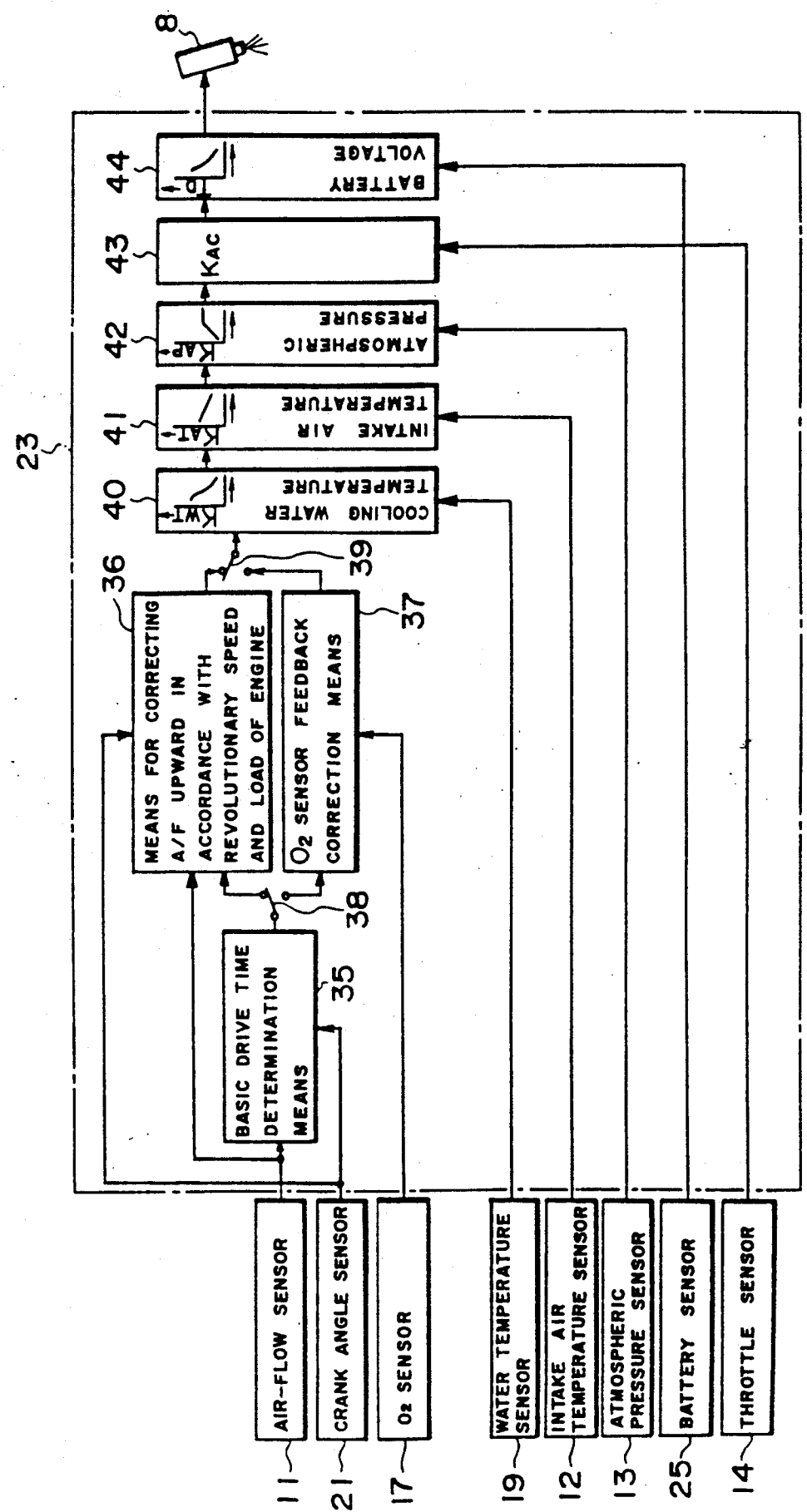
Figure 49:
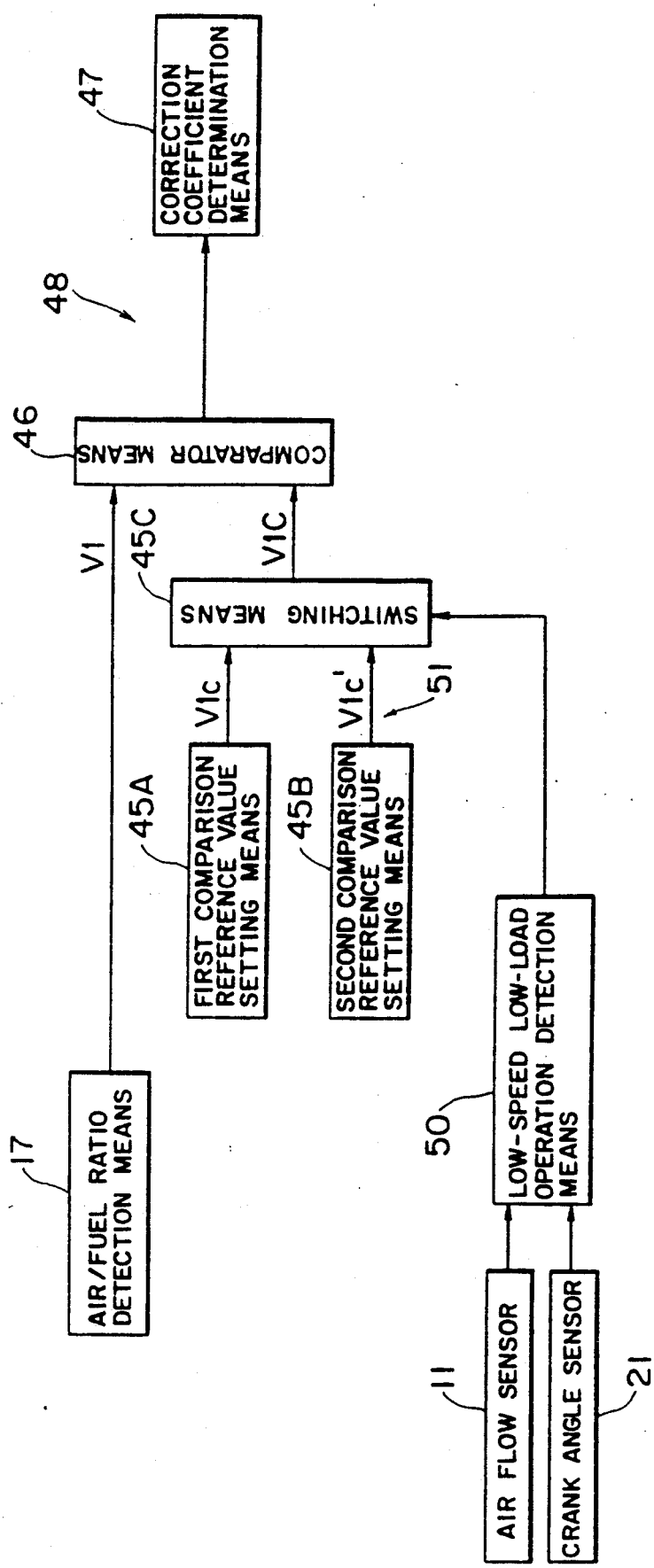
Figure 50:
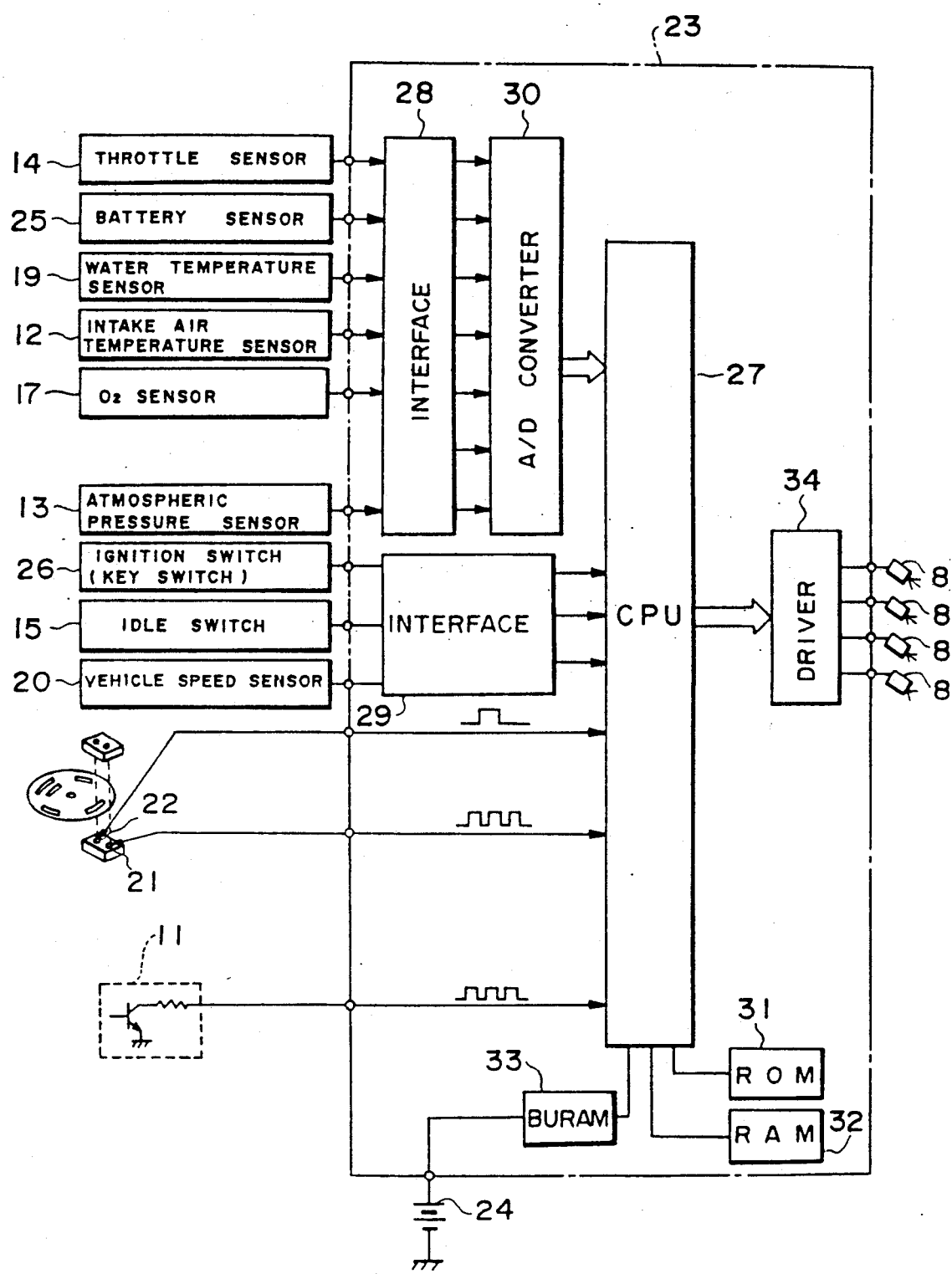
Figure 51:
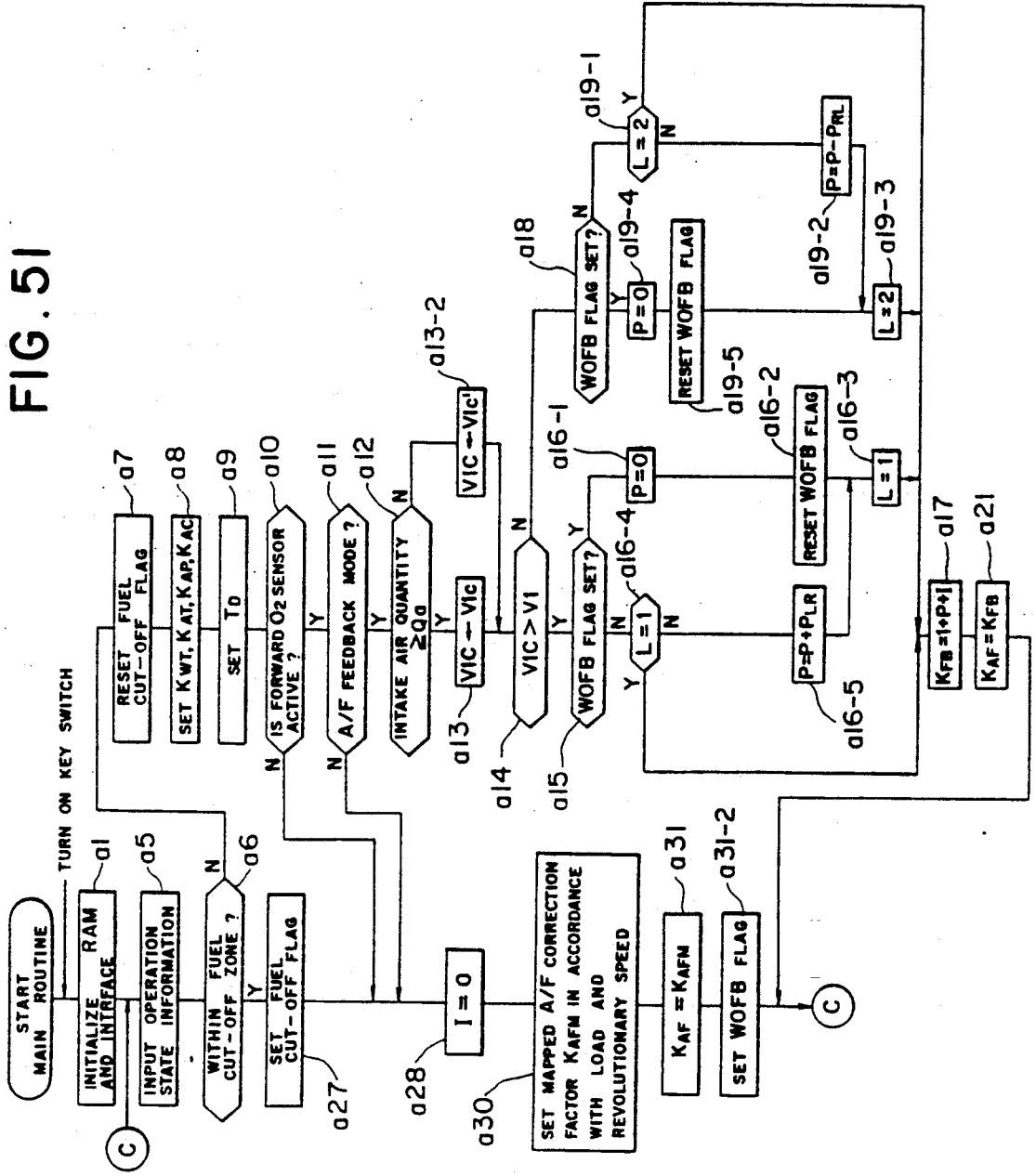
Figure 52A:
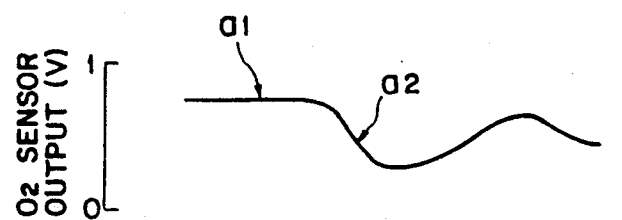
FIGS. 52(a) through 52(c) diagrammatically show effects of a conventional control system upon acceleration.
Figure 52B:
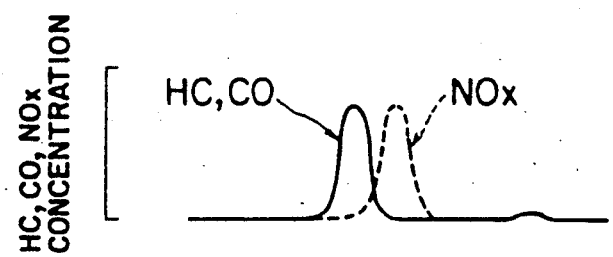
Figure 52C:
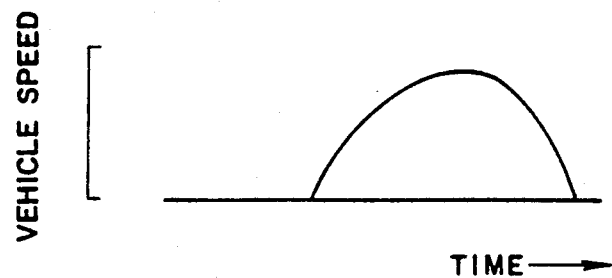

This fourth embodiment is directed to the so-called $O_2$ feedback control that as shown in FIG. 47, the downstream $O_2$ sensor 18 is not provided, only the $O_2$ sensor 17 is provided in the exhaust manifold, i.e., on the upstream side of the catalytic converter 9, and the output of the $O_2$ sensor 17 is fed back. In the fourth embodiment, the response delay times, integral gains, proportional gains and rich/lean-judging first reference value are corrected on the basis of the deviation $\Delta V$ of the detection value V2 from the downstream $O_2$ sensor 18 from the reference value V2c, whereby a flow computation such as that shown in FIG. 51 is performed by a control system such as that illustrated in FIG. 49 without correcting the control of the air/fuel ratio. As a consequence, the air/fuel ratio is controlled based on the results of a comparison between a detection value V1 from the $O_2$ sensor 17 and the predetermined reference value V1c. As this reference value, V1c of about 0.5 volt by way of example from the first reference value setting means 45A is chosen in operation states other than the low-speed and low-load operation state, but V1c' of about 0.3 volt by way of example from the second reference value setting means 45B is chosen in the low-speed and low-load operation.

The fourth embodiment also makes it possible to shift the reference value, which is to be compared with a detection value from the $O_2$ sensor 17, to the lean air/fuel ratio side in the small intake-air-quantity operation state while performing $O_2$ feedback control. It is therefore possible to avoid deterioration of the efficiency of purification for HC, CO and NOx by the catalytic converter even when accelerated from the small intake-air-quantity operation state.

Further, the present invention can be applied to any system which performs a feedback control by one or more $O_2$ sensors. Needless to say, this invention can be applied not only to engine systems of the MPI system but also to engine systems of the SPI (single point fuel injection) system.

What is claimed is:

1. An air/fuel ratio control system for an internal combustion engine, comprising:

a first air/fuel ratio detection means arranged on an upstream side of a catalytic converter so as to detect the air/fuel ratio of the internal combustion engine from components of exhaust gas, said catalytic converter being provided in an exhaust system of the internal combustion engine and adapted to clean the exhaust gas;

a second air/fuel ratio detection means arranged in the exhaust system and having a detection response speed slower than the said air/fuel ratio detection a means for controlling the air/fuel ratio of the internal combustion engine on the basis of results of a comparison between a detection value from said first air/fuel ratio detection means and a predetermined first reference value;

a means for effecting a correction to the control of the air/fuel ratio by said air/fuel ratio control means on the basis of results of a comparison between a detection value from said second air/fuel ratio detection means and a predetermined second reference value;

a means for shifting the first reference value to a lean air/fuel ratio side in a specific operation state of the internal combustion engine; and a means for prohibiting the correction by the air/fuel ratio controlling means in the specific operation state.

2. The system of claim 1, wherein the air/fuel ratio of the internal combustion engine is controlled to stoichiometric air/fuel ratio on the basis of the results of the comparison between the detection value from said first air/fuel ratio detection means and the first reference value.

3. The system of claim 2, wherein the specific operation state is a low-load operation state.

4. The system of claim 3, wherein the low-load operation state is an idling operation state.

5. The system of claim 3, wherein the low-load operation state is a low-speed and low-load operation state.

6. The system of claim 2, wherein the specific operation state is a small intake-air-quantity operation state.

7. The system of claim 6, further comprising a means for detecting the quantity of intake air, whereby the internal combustion engine is judged to be in the small intake-air-quantity operation state when an output from said intake-air-quantity detection means falls below a predetermined value.

8. The system of claim 7, wherein said intake-air-quantity detection means is a Karman sensor which outputs a pulse signal of a frequency based on Karman vortices of intake air and corresponding to information on the quantity of the intake air.

9. The system of claim 1, wherein said second air/fuel ratio detection means is arranged on a downstream side of the catalytic converter.

10. The system of claim 1, wherein said second air/fuel ratio detection means is exposed to exhaust gas via an exhaust gas cleaning catalyst, is formed integrally with said first air/fuel detection means, and is arranged on an upstream side of the catalytic converter.

11. The system of claim 1, wherein at least one of response delay time, integral gain, proportional gain, and the first reference value to be compared with the detection value from said first air/fuel ratio detection means is corrected to effect the correction to the control of the air/fuel ratio by said air/fuel ratio control means on the basis of the results of the comparison between the detection value from said second air/fuel ratio control means and the second reference value.

12. The system of claim 11, wherein the correction is effected when a predetermined sampling signal is generated.

13. The system of claim 12, wherein the sampling signal is generated whenever the detection value from said first air/fuel ratio detection means changes across the first reference value to be compared with the detection value.

* * * * *